United States Patent
Manzo et al.

(10) Patent No.: US 7,367,973 B2
(45) Date of Patent: May 6, 2008

(54) ELECTRO-SURGICAL INSTRUMENT WITH REPLACEABLE END-EFFECTORS AND INHIBITED SURFACE CONDUCTION

(75) Inventors: Scott Manzo, Shelton, CT (US); Joseph P. Orban, III, Norwalk, CT (US); Andris Ramans, Sunnyvale, CA (US); Matt Williams, Walnut Creek, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 257 days.

(21) Appl. No.: 10/611,411

(22) Filed: Jun. 30, 2003

(65) Prior Publication Data

US 2004/0267254 A1    Dec. 30, 2004

(51) Int. Cl.
*A61B 18/18* (2006.01)

(52) U.S. Cl. .............................. 606/41; 606/45; 606/1; 606/49; 606/167; 604/22

(58) Field of Classification Search ............ 606/27–52, 606/1, 167; 604/22; 901/30
See application file for complete search history.

(56) References Cited

U.S. PATENT DOCUMENTS

| | | | |
|---|---|---|---|
| 5,429,596 A | 7/1995 | Arias et al. | |
| 5,496,315 A * | 3/1996 | Weaver et al. | 606/41 |
| 5,630,812 A * | 5/1997 | Ellman et al. | 606/41 |
| 5,649,956 A | 7/1997 | Jensen et al. | |
| 5,662,647 A * | 9/1997 | Crow et al. | 606/41 |
| 5,792,135 A | 8/1998 | Madhani et al. | |
| 5,797,900 A | 8/1998 | Madhani et al. | |
| 5,807,378 A | 9/1998 | Jensen et al. | |
| 5,808,665 A | 9/1998 | Green | |
| 5,976,122 A | 11/1999 | Madhani et al. | |
| 6,004,509 A | 12/1999 | Dey et al. | |
| 6,007,570 A * | 12/1999 | Sharkey et al. | 607/96 |
| 6,090,107 A * | 7/2000 | Borgmeier et al. | 606/41 |
| 6,102,909 A | 8/2000 | Chen et al. | |
| 6,132,441 A | 10/2000 | Grace | |
| 6,206,903 B1 | 3/2001 | Ramans | |
| 6,309,397 B1 | 10/2001 | Julian et al. | |
| 6,312,435 B1 | 11/2001 | Wallace et al. | |
| 6,331,181 B1 * | 12/2001 | Tierney et al. | 606/130 |

(Continued)

FOREIGN PATENT DOCUMENTS

WO    WO 99/50721 A1    10/1999

OTHER PUBLICATIONS

U.S. Appl. No. 09/378,173, filed Aug. 20, 1999.

(Continued)

*Primary Examiner*—Roy D. Gibson
*Assistant Examiner*—Pete Vrettakos

(57) ABSTRACT

Improved robotic surgery end-effectors include at least one insulation material for inhibiting surface conduction of electrical current in a proximal direction, from a distal active electrode toward the proximal end of the end-effector and toward the rest of the surgical instrument itself. Some embodiments include two layers of insulation to further prevent proximally-directed current. By inhibiting proximal current flow, the end-effectors prevent unwanted patient burns as well as electricity-related wear and tear in and around the area where the end-effector is coupled with the rest of the surgical instrument. In various embodiments, such end-effectors are preferably removably coupleable with a robotic surgical instrument.

30 Claims, 18 Drawing Sheets

U.S. PATENT DOCUMENTS

| | | |
|---|---|---|
| 6,394,998 B1 | 5/2002 | Wallace et al. |
| 6,424,885 B1 | 7/2002 | Niemeyer et al. |
| 6,436,107 B1 | 8/2002 | Wang et al. |
| 6,464,701 B1 | 10/2002 | Hooven et al. |
| 6,491,691 B1 | 12/2002 | Morley et al. |
| 6,491,701 B2 * | 12/2002 | Tierney et al. ............... 606/130 |
| 2002/0120363 A1 | 8/2002 | Salisbury et al. |
| 2002/0177843 A1 | 11/2002 | Anderson et al. |
| 2002/0188293 A1 | 12/2002 | Manzo |
| 2003/0036748 A1 | 2/2003 | Cooper et al. |

OTHER PUBLICATIONS

U.S. Appl. No. 09/399,457, filed Sep. 17, 1999.
U.S. Appl. No. 09/626,527, filed Jul. 27, 2000.
U.S. Appl. No. 60/111,711, filed Dec. 8, 1998.
U.S. Appl. No. 60/111,713, filed Dec. 8, 1998.
U.S. Appl. No. 60/285,485, filed Apr. 19, 2001.
U.S. Appl. No. 60/431,636, filed Dec. 6, 2002.
Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

* cited by examiner

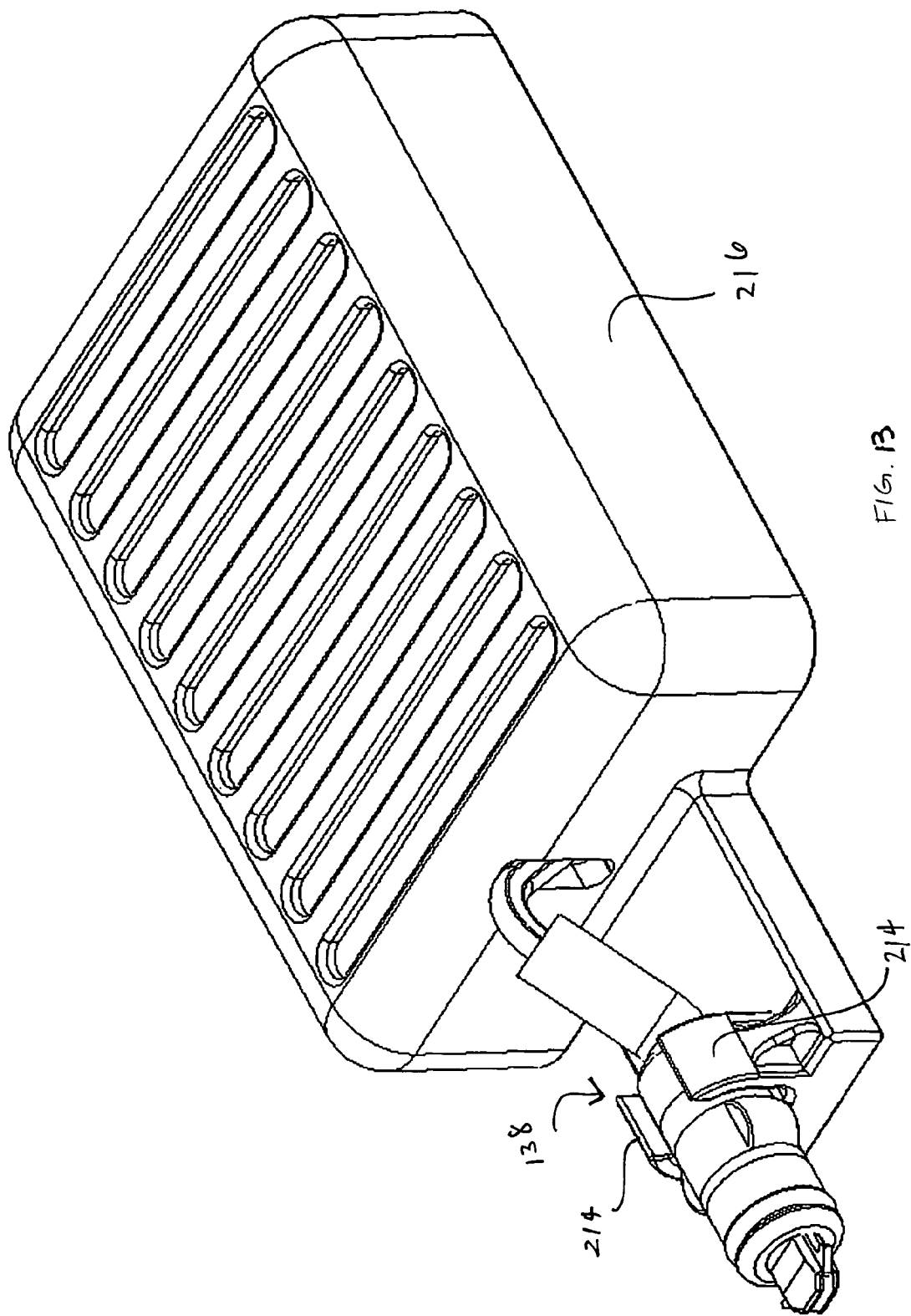

ELECTRO-SURGICAL INSTRUMENT WITH REPLACEABLE END-EFFECTORS AND INHIBITED SURFACE CONDUCTION

BACKGROUND OF THE INVENTION

The present invention generally relates to surgical apparatus and methods. More specifically, the invention relates to an electro-surgical instrument with inhibited surface conduction and methods for use with a robotic surgical system.

Minimally invasive surgical techniques generally reduce the amount of extraneous tissue damage during surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. Patient recovery times, patient discomfort, surgical side effects, and time away from work can also be reduced by increasing the use of minimally invasive surgery.

In theory, a significant number of surgical procedures could potentially be performed by minimally invasive techniques to achieve the advantages just described. Only a small percentage of procedures currently use minimally invasive techniques, however, because certain instruments, systems and methods are not currently available in a form for providing minimally invasive surgery.

Traditional forms of minimally invasive surgery typically include endoscopy, which is visual examination of a hollow space with a viewing instrument called an endoscope. One of the more common forms of endoscopy is laparoscopy, which is visual examination and/or treatment of the abdominal cavity. In traditional laparoscopic surgery a patient's abdominal cavity is insufflated with gas, and cannula sleeves are passed through small incisions in the musculature of the patient's abdomen to provide entry ports through which laparoscopic surgical instruments can be passed in a sealed fashion. Such incisions are typically about ½ inch (about 12 mm) in length.

Laparoscopic surgical instruments generally include a laparoscope for viewing the surgical field and working tools defining end-effectors. Typical surgical end-effectors include, for example, clamps, graspers, scissors, staplers, hooks, electrocautery devices, needle holders and the like. The working tools are similar to those used in conventional (open) surgery, except that the working end or end-effector of each tool is separated from its handle by a long extension tube, typically of about 12 inches (about 300 mm) in length, for example, so as to permit the surgeon to introduce the end-effector to the surgical site and to control movement of the end-effector relative to the surgical site from outside a patient's body.

To perform a surgical procedure, a surgeon typically passes the working tools or instruments through the cannula sleeves to the internal surgical site and manipulates the instruments from outside the abdomen by sliding them in and out through the cannula sleeves, rotating them in the cannula sleeves, levering (i.e., pivoting) the instruments against the abdominal wall and actuating the end-effectors on distal ends of the instruments from outside the abdominal cavity. The instruments normally pivot around centers defined by the incisions which extend through the muscles of the abdominal wall. The surgeon typically monitors the procedure by means of a television monitor which displays an image of the surgical site captured by the laparoscopic camera. Typically, the laparoscopic camera is also introduced through the abdominal wall so as to capture the image of the surgical site. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Although traditional minimally invasive surgical instruments and techniques like those just described have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end-effector. Furthermore, coordination of the movement of the end-effector of the instrument as viewed in the image on the television monitor with actual end-effector movement is particularly difficult, since the movement as perceived in the image normally does not correspond intuitively with the actual end-effector movement. Accordingly, lack of intuitive response to surgical instrument movement input is often experienced. Such a lack of intuitiveness, dexterity and sensitivity of endoscopic tools has been found to be an impediment in the increased use of minimally invasive surgery.

Minimally invasive robotic (or "telesurgical") surgical systems have been developed to increase surgical dexterity and allow a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient while viewing the end-effector movement on the visual display during the surgical procedure. Typically while viewing a three-dimensional image of the surgical site on the visual display, the surgeon performs the surgical procedures on the patient by manipulating master control devices at the remote location, which master control devices control motion of the remotely controlled instruments.

Such a telesurgery system is often provided with at least two master control devices (one for each of the surgeon's hands), which are normally operatively associated with two robotic arms on each of which a surgical instrument is mounted. Operative communication between master control devices and associated robotic arm and instrument assemblies is typically achieved through a control system. The control system typically includes at least one processor which relays input commands from the master control devices to the associated robotic arm and instrument assemblies and from the arm and instrument assemblies to the associated master control devices in the case of, e.g., force feedback, or the like. One example of a robotic surgical system is the DA VINCI® system available from Intuitive Surgical, Inc. of Mountain View, Calif.

One type of end-effector which is often advantageous for use with a robotic surgical system is an electro-surgical end-effector, such as an electrocautery device. Electro-surgical devices, such as monopolar and bipolar devices, electrocautery scissors, hooks or jaws and the like, are commonly used in laparoscopic surgery and conventional surgery to cut tissue and/or coagulate small blood vessels. Thus, electro-surgical end-effectors have been developed for use with robotic surgical systems. Although many such electro-surgical end-effectors are quite effective, there are ways in which such devices may be improved.

One shortcoming of currently available end-effectors is that they are not optimally designed to inhibit conduction of current from the active electrode at the distal end of the effector back toward proximal parts of the electro-surgical instrument. Current conducted proximally from the active electrode may melt or otherwise damage one or more proximal parts of the electro-surgical instrument. Such a proximally-transmitted current may also increase the temperature of a proximal portion of the instrument and thus cause an unwanted patient burn at a location apart from the active electrode.

Another possible shortcoming of currently available devices is that the end-effector is typically permanently connected to the rest of the electro-surgical instrument. Although such permanently connected end-effectors work well, the permanent connection makes cleaning of the electrode difficult, often requiring the entire electro-surgical instrument to be autoclaved or otherwise cleaned. Such permanently attached electrodes may also sustain larger amounts of wear and tear before being replaced, which may compromise performance of the end-effector.

Therefore, a need exists for improved electro-surgical instruments and end-effectors for use with a robotic surgical system. Improved end-effectors would include means for inhibiting surface conduction of current from a distal active electrode to more proximal portions of the end-effector and to the electro-surgical instrument. Ideally such end-effectors would be available either permanently attached to an electro-surgical instrument or removably attachable to an instrument. At least some of these objectives will be met by the present invention.

BRIEF SUMMARY OF THE INVENTION

Improved robotic surgery end-effectors include at least one insulation material for inhibiting surface conduction of electrical current in a proximal direction, from a distal active electrode toward the proximal end of the end-effector and toward the rest of the surgical instrument itself. Some embodiments include two layers of insulation to further prevent proximally-directed current. By inhibiting proximal current flow, the end-effectors prevent unwanted patient burns as well as electricity-related wear and tear in and around the area where the end-effector is coupled with the rest of the surgical instrument. In various embodiments, such end-effectors may be preferably removably coupleable with a robotic surgical instrument.

In one aspect of the invention, an end-effector device for use with an electrosurgical instrument for robotic surgery includes at least one active electrode at a distal end of the device, coupling means adjacent a proximal end of the device for coupling the device with the electrosurgical instrument, and at least one insulation material disposed at least partially around the active electrode for inhibiting conduction of electrical current from the active electrode to the electrosurgical instrument. The active electrode may be a simple electrode or may comprise any suitable electrode device, such as but not limited to a scalpel blade, a beaver blade, a hook, a spatula, movable jaws, scissors, a needle point, hockey stick, dissectors, or a probe. In some embodiments, the active electrode transmits radiofrequency energy, although any other form of energy may be used, such as microwave energy or the like.

The coupling means may provide for either removable coupling or permanent coupling of the device with the electrosurgical instrument. As noted above, it is preferred that the end-effector is removably coupleable to conveniently permit the end-effector to be easily mounted and de-mounted for replacement or refurbishing as well as to facilitate convenient sterilization of the surgical instrument. The coupling means may comprise mechanical attachments. In one embodiment, the coupling means comprise threading within an end-effector sleeve for attachment with complimentary threading on a mating component permanently attached to the electrosurgical instrument. In another embodiment, the coupling means comprise at least one spring tab or latching member on the proximal end of the device for attachment with at least one protrusion within a housing permanently attached to the electrosurgical instrument. Still further, the coupling means may comprise alternative mechanisms such as a bayonet assembly. It will be appreciated that the mechanical coupling provides both an axial as well as rotational constraint. The removable end-effector may further be disposable, wherein the device may further comprise a lockout feature (e.g., ring) associated with the coupling means for preventing any re-use of the disposable end-effector.

The coupling means may additionally comprise electrical attachments. In one embodiment, the electrical coupling means comprise an electrical connector on the proximal end of the device for electrical connection with a transmission member via a spring compression member of the electrosurgical instrument. In another embodiment, the electrical coupling means comprise an electrical connector on the proximal end of the device for electrical connection with a transmission member via a gripping member of the electrosurgical instrument. In still a further embodiment, the electrical coupling means comprise an electrical connector on the proximal end of the device and an electrical tab on the proximal end of the electrical connector for electrical connection with a transmission member via an electrical platform of the electrosurgical instrument. At least one o-ring or silicone potting is associated with the coupling means to seal the electrical connection.

In some embodiments, the at least one insulation material includes a first insulation layer disposed at least partially around the active electrode and a second insulation layer disposed at least partially around the first layer or the active electrode. Both the first layer and the second layer may be made of any suitable material or materials. For example, in one embodiment the first layer may include, but is not limited to, ceramic material, glass, silicone, polypropylene, fluoropolymer (e.g., FEP fluorinated ethylene propylene), or insulating plastic. In some embodiments, the second layer may include, but is not limited to, ceramic material, glass, silicone, polypropylene, fluoropolymer, or insulating plastic. Insulation may be disposed around all or part of the active electrode in any suitable configuration, shape, pattern or amount. In one embodiment, for example, the first layer of insulation comprises a first insulation material completely encircling part of the active electrode, and the second layer comprises a second insulation material completely encircling the first layer and abutting the electrosurgical instrument. Any combination of insulation materials and any configuration of insulation materials on or around the active electrode is contemplated within the scope of the invention.

In another aspect, an electrosurgical instrument for use with a robotic surgical system includes an elongate shaft having a proximal end and a distal end, an end-effector removably coupled with the distal end of the shaft, the end-effector having at least one active electrode and at least one insulation material disposed at least partially around the active electrode for inhibiting conduction of electrical current from the active electrode to the electrosurgical instrument, and an interface coupleable to the proximal end of the shaft, the interface removably connectable to the robotic surgical system.

Again, in various embodiments the active electrode may comprise a scalpel blade, a beaver blade, a hook, a spatula, movable jaws, scissors, a needle point, hockey stick, dissectors, a probe or any other suitable device. The end-effector may further comprise an end-effector sleeve having threading for attachment with complimentary threading on a mating component permanently attached to the distal end of the shaft. Alternatively, the end-effector may further comprise at least one spring tab or latching member for attachment with at least one protrusion within a housing permanently attached to the distal end of the shaft. In some embodiments, the insulation material includes a first insulation layer disposed at least partially around the active electrode and a second insulation layer disposed at least partially around the first layer or the active electrode. Either of these layers, or any other layers of insulation used, may comprise any suitable material or combination of materials, and the insulation material(s) may be disposed on and/or around the active electrode in any suitable configuration, as described above In yet another aspect, a method of making an end-effector device for use with an electrosurgical instrument for robotic surgery involves assembling the end-effector device, with the device having at least one active electrode, applying a first insulator to at least part of the active electrode to inhibit surface conduction of current from the active electrode back to the electrosurgical instrument, and applying a second insulator to at least part of the active electrode or the first insulator to further inhibit surface conduction from the active electrode back to the electrosurgical instrument. In some embodiments, applying the first insulator involves applying a glass insulator around a portion of the active electrode. The glass insulator may have a pre-molded shape to fit within a corresponding shape on the active electrode. Optionally, the glass insulator may be applied to the active electrode via any suitable method, such as soldering, fusing, or the like. The second insulator may similarly be applied by any suitable method. For example, in one embodiment a ceramic insulator is disposed around a portion of the active electrode immediately proximal to the glass insulator. In another embodiment, applying the first insulator comprises coating a length of the active electrode with a ceramic insulator. Optionally, applying the second insulator comprises covering at least a portion of the ceramic insulator with a fluoropolymer insulator. In some embodiments, either the first insulator, the second insulator or both abuts the electrosurgical instrument.

In another aspect, a method of performing a robotic surgical procedure involves connecting a surgical instrument to a robotic surgical system, the surgical instrument having an elongate shaft at a distal end of which an end-effector is coupled, passing the end-effector of the surgical instrument through an entry port in a patient body, engaging tissue with an active electrode of the end-effector, and delivering electrical energy to the tissue with the active electrode while inhibiting conduction of the electrical energy from the active electrode toward the distal end of the elongate shaft. In some embodiments, the method also involves removably coupling the end-effector with the surgical instrument.

In some embodiments, such removably coupling of the end-effector does not require a coupling tool, thus facilitating coupling and removing the end-effector. Some embodiments of the method further include disabling the end-effector after the robotic surgical procedure is performed. Such a disabling step may prevent overuse of a worn or damaged end-effector and/or contamination of an end-effector between patients. In many embodiments, as discussed previously, delivering the electrical energy while inhibiting conduction is achieved via at least one layer of insulation disposed on at least part of the active electrode. In some embodiments, the insulation comprises two layers of insulation. Typically, sealing of the layers of the insulation may be carried out with a silicone adhesive. Sealing the insulation layer to the active electrode may carried out with conventional over-molding processes.

In another aspect of the present invention, an electrosurgical instrument for use with a robotic surgical system may comprise an elongate shaft having a proximal end and a distal end. An end-effector may be removably coupled with the distal end of the shaft, the end-effector comprising at least one active electrode, the active electrode preferably comprising a hook or spatula. An end-effector sleeve may be disposed at least partially around the active electrode, the sleeve having threading for attachment with complimentary threading on a mating component permanently attached to the distal end of the shaft. An electrical connector may be disposed within the sleeve for electrical connection with a transmission member via a gripping member of the mating component. An interface may further be coupleable to the proximal end of the shaft, the interface removably connectable to the robotic surgical system. In such an embodiment, the sleeve preferably comprises an insulation material for inhibiting conduction of electrical current from the active electrode to the electrosurgical instrument.

In yet another aspect of the present invention, an electrosurgical instrument for use with a robotic surgical system may comprise an elongate shaft having a proximal end and a distal end. An end-effector may be permanently coupled with the distal end of the shaft, the end-effector comprising an electrocautery hook or spatula. A first insulation layer may be disposed at least partially around the hook or spatula so as to inhibit conduction of electrical current from the active electrode to the electrosurgical instrument. A second insulation layer may be disposed at least partially around the first layer or the hook or spatula so as to further inhibit conduction of electrical current from the active electrode to the electrosurgical instrument. An interface may be coupleable to the proximal end of the shaft, the interface removably connectable to the robotic surgical system.

In still another aspect of the present invention, a robotical surgical system may comprise a robotic arm having an instrument holder. An electrocautery instrument may be detachably mountable on the instrument holder. The electrocautery instrument has a proximal portion for engaging the instrument holder, an elongate shaft extending from the proximal portion to a distal end, and an end-effector removably coupled with the distal end of the shaft. The end-effector has at least one active electrode and at least one insulation material disposed at least partially around the active electrode. An electrosurgical generator is further included to transmit electrosurgical energy to the active electrode.

In a still further aspect of the present invention, an electrocautery end-effector is provided for use with an electrosurgical instrument comprising a shaft, an end-effector removably coupled to a distal end of the shaft, and an interface coupleable to a proximal end of the shaft. The electrosurgical instrument is for use with a robotic surgery system. The electrocautery end-effector comprises an electrocautery hook or spatula. An end-effector sleeve is disposed at least partially around the hook or spatula, the sleeve having threading for attachment with complimentary threading on a mating component permanently attached to the distal end of the shaft. An electrical connector is within the sleeve for electrical connection with a transmission member via a gripping member of the mating component. At least one insulation material is disposed at least partially around the hook or spatula for inhibiting conduction of electrical current from the active electrode to the electrosurgical instrument.

BRIEF DESCRIPTION OF THE DRAWINGS

FIG. 13 is a perspective illustration of a disposable end-effector device housed in a disposable housing for storage before use, in accordance with one embodiment of the present invention.

DETAILED DESCRIPTION

The present invention provides devices and methods for use in robotically controlled minimally invasive surgical operations. In particular, the present invention relates to improved end-effectors and electrosurgical instruments for use in robotic surgery. The end-effectors generally include means for inhibiting electrical current flow proximally from an active electrode toward the area of coupling between the end-effector and the rest of the electrosurgical instrument. The means for current flow inhibition often include one or more insulation materials, and in some embodiments an end-effector includes two layers of insulation material(s). In various embodiments, such end-effectors may be either removable coupleable with the electrosurgical instrument or permanently coupled with the instrument. Such end-effectors enhance methods of performing a minimally invasive surgical procedure while preventing unwanted and unintended burning of the patient, collateral tissue damage, melting of the instrument, damage to the robotic surgical system or the like.

Generally, the end-effectors and electrosurgical instruments of the present invention are capable of treating tissue of an organism with the use of heat produced by electrical energy, though any other suitable form of energy may be used, such as ultrasound, microwave or laser energy. In some embodiments, an end-effector may be configured as an electrode or cautery hook that applies current to living tissue at a surgical site. Optionally, the end-effector may comprise a combined cutting, shearing, clamping, stapling, or grasping device or any other suitable electrosurgery end-effector. As the tissue current is conducted through the tissue, the tissue temperature rises, ultimately causing desiccation, cutting, cauterization, and/or coagulation of the treatment tissue (i.e., blood vessels and the like). The electrosurgical treatment may further reduce bleeding of tissue by cauterizing tissue and coagulating blood, or achieve various other desired effects on the treatment tissue.

Figure 1:
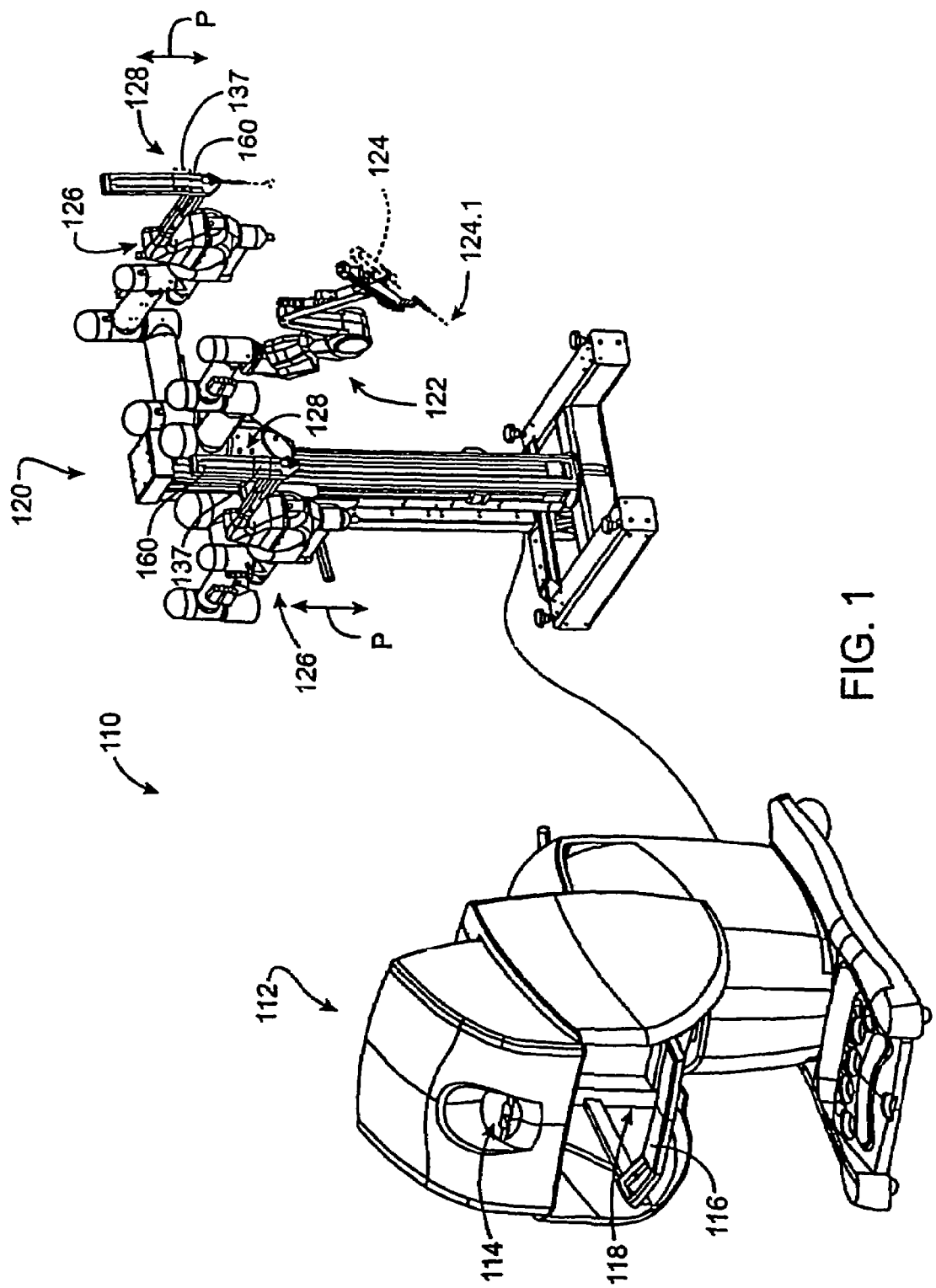
FIG. 1 is a perspective illustration of a robotic surgical system with which various embodiments of the present invention may be used.

Referring now to FIG. 1, a robotic surgical system 110 generally includes a user-operated control station or "surgeon's console" 112 and a surgical work station or "cart" 120. The control station 112 includes an image display module 114 for displaying an image of a surgical site, a support 116 on which an operator may rest his/her forearms, and a space 118 where two master control devices are located (not shown). When using control station 112, a surgeon or other user typically sits in a chair in front of control station 112, views the surgical site through the display module 114, and grips the master controls one in each hand while resting the forearms on support 116. An exemplary robotic surgical system as described in FIG. 1 is the DA VINCI® system available from Intuitive Surgical, Inc. of Sunnyvale, Calif.

Control station 112 is generally coupled to cart 120 such that commands from the master controls may be transmitted to the cart 120. In use, cart 120 is positioned adjacent a patient requiring surgery and is then normally caused to remain stationary until a surgical procedure to be performed by means of surgical system 110 has been completed. Cart 120 typically has wheels or castors to render it mobile. Control station 112 is typically positioned remote from cart 120 and in some embodiments may be separated from cart 120 by a great distance, for example miles away, but will typically be used within an operating room with the cart 120.

In various embodiments, cart 120 includes at least three robotic arm assemblies 122, 126, 126, one of which is configured to hold an image capture device 124 and the others of which are configured to hold surgical instruments 128. Alternatively, the cart may include more or fewer than three robotic arm assemblies and the robotic arm assemblies may be configured to hold any suitable tool, instrument, imaging device and/or the like. Image capture device 124 may include any suitable device, such as an endoscope, fiber optic camera, or the like. Image capture device 124 generally includes an object viewing end 124.1 at a remote end of an elongate shaft configured to enable the viewing end 124.1 to be inserted through an entry port in a patient's body to capture an image of the surgical site.

Coupling of cart 120 to control station 112 generally enables display module 114 to display an image captured by image capture device 124. Coupling of cart 120 to control station 112 also typically allows each of the master controls on the control station 112 (not shown) to control one robotic arm assembly 126 and one surgical instrument 128. In various embodiments, each master control may alternatively be used to control more than one robotic arm assembly 126 and/or more than one surgical instrument 128.

Surgical instruments 128 on the robotic arm assemblies 126 typically include elongate shafts, with proximal and distal ends. End-effectors are generally mounted on wrist-like mechanisms 100 pivotally mounted on the distal ends of the shafts 131, for enabling the instruments 128 to perform one or more surgical tasks. Generally, the elongate shafts of surgical instruments 128 allow the end-effectors to be inserted through entry ports in a patient's body so as to access the internal surgical site. Movement of the end-effectors is generally controlled via master controls on the control center 112.

Figure 2:
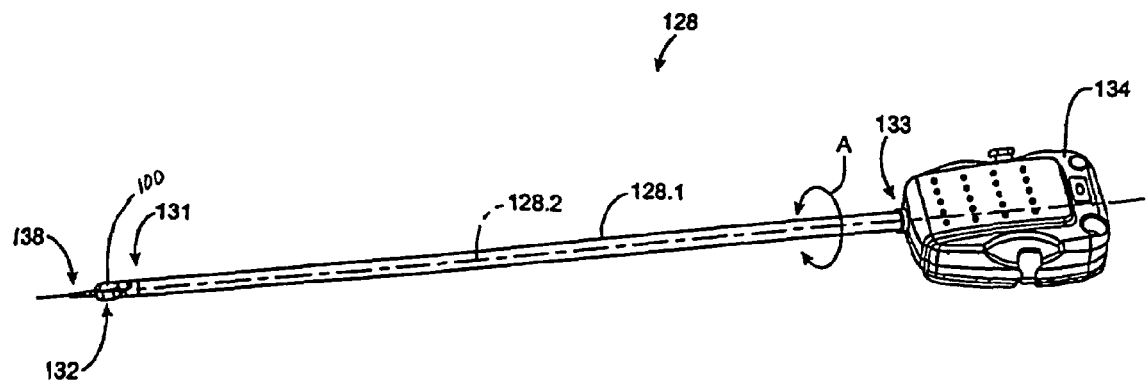
FIG. 2 is a perspective illustration of a robotic surgical tool which may be used with the robotic surgical system of FIG. 1.

Referring now to FIG. 2, surgical instrument 128 generally includes an elongate shaft 128.1 having a proximal end 133 and a distal end 131, a pivot 132, an end-effector 138 disposed at the distal end, and an instrument base 134 disposed at the proximal end. Base 134 is generally configured to releasably engage an interface member of the robotic surgical system, such as robotic surgical system 110 in FIG. 1. In general, instrument 128 is engaged with the system via base 134 (base not shown in FIG. 1) such that instrument 128 is releasably mountable on a carriage 137 which can be driven to translate along a linear guide formation 160 of the arm 126 in the direction of arrows P.

With reference to FIG. 2, shaft 128.1 is rotatably mounted on base 134 for rotation about an axis 128.2 extending longitudinally along the shaft 128.1 as indicated by the arrows A. Thus, when mounted on an arm assembly 126, end-effector 138 may have a plurality of degrees of freedom of movement relative to manipulator arm 126, in addition to actuation movement of the end-effector 138 itself. The instrument may be translated along an insertion axis (Arrows P in FIG. 1). Typically, the instrument degrees of freedom include rotation about the axis 128.2 as indicated by arrows A, and in the case of instruments 128 including pivots 132, angular displacement as a whole about pivot 132 as indicated by arrow D. Alternatively, the distal pivoting degree of freedom may be omitted. A single pivot wrist, a multi-pivot wrist, a distal roll joint mechanism, or other joints or wrist-like mechanisms 100 may be included in any embodiments of the present invention to provide additional operational degrees of freedom to the end-effector 138. Movement of end-effector 138 relative to manipulator arm 126 is controlled by appropriately positioned actuators, such as electric motors, or the like, which respond to inputs from an associated master control at the control station 112, so as to drive the end-effector 138 to a required orientation as dictated by movement of the associated master control.

Figure 3:
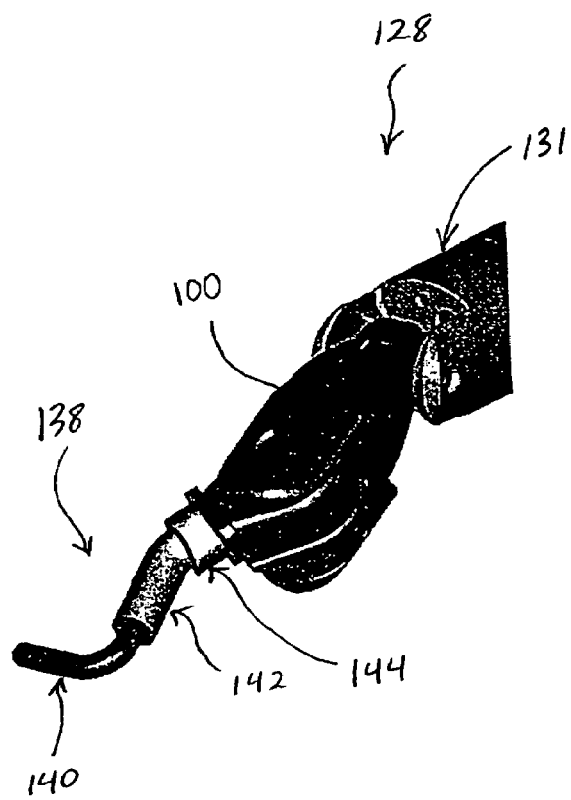
FIG. 3 is a perspective illustration of a distal end of a robotic surgical instrument with an end-effector having insulation layers, in accordance with one embodiment of the present invention.

Referring now to FIG. 3, distal end 131 of instrument 128 is shown, coupled with one embodiment of end-effector 138. As mentioned above, end-effector 138 may suitably include an active electrode 140 and one or more insulation materials 142, 144 disposed on and/or around active electrode 140 to prevent electric current from traveling or arcing proximally from active electrode 140 to the rest of instrument 128. The active electrode may be a simple electrode or hook device (as shown in FIG. 3) or may comprise any suitable electrode device, such as but not limited to a scalpel blade, a beaver blade, a spatula, movable jaws, scissors, a probe and/or the like. In some embodiments, the active electrode transmits radiofrequency energy, although any other form of energy may be used, such as ultrasound energy, microwave energy, laser energy, photoablative energy or the like.

In some embodiments, insulation materials include a first insulation layer 142, which is generally applied directly to active electrode 140, and a second insulation layer 144, which may be applied direction to active electrode 140, may overlap first insulation layer 142, or both. Generally, both first insulation layer 142 and second insulation layer 144 may include any suitable insulation material or combination of materials and may be disposed along active electrode 140 in any suitable configuration, shape, pattern or the like. For example, in one embodiment first layer 142 may include, but is not limited to, a ceramic material, glass and/or silicone, and second layer 144 may be made of FEP material. Insulation layers 142, 144 may be disposed around all or part of active electrode 140 in any suitable configuration, shape, pattern or amount. In one embodiment, for example, first layer 142 comprises a first insulation material completely encircling part of active electrode 140, and second layer 144 comprises a second insulation material completely encircling first layer 142. Any combination of insulation materials 142, 144 and any configuration of insulation materials 142, 144 on or around active electrode 140 is contemplated within the scope of the invention. Generally, insulation materials 142, 144 help prevent electric current from flowing and/or arcing proximally to cause unwanted patient burns and burning, melting or other wear and tear of end-effector 138 and/or instrument 128.

Figure 4A:
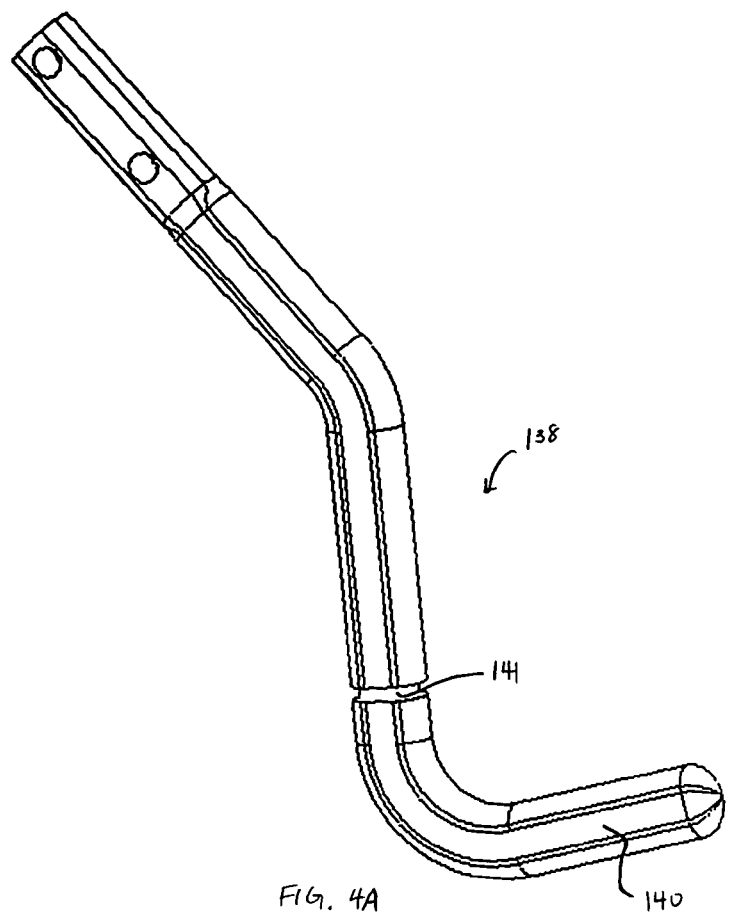
FIGS. 4A-4D are perspective illustrations of an insulated end-effector device in various stages of manufacture, in accordance with one embodiment of the present invention.
Figure 4B:
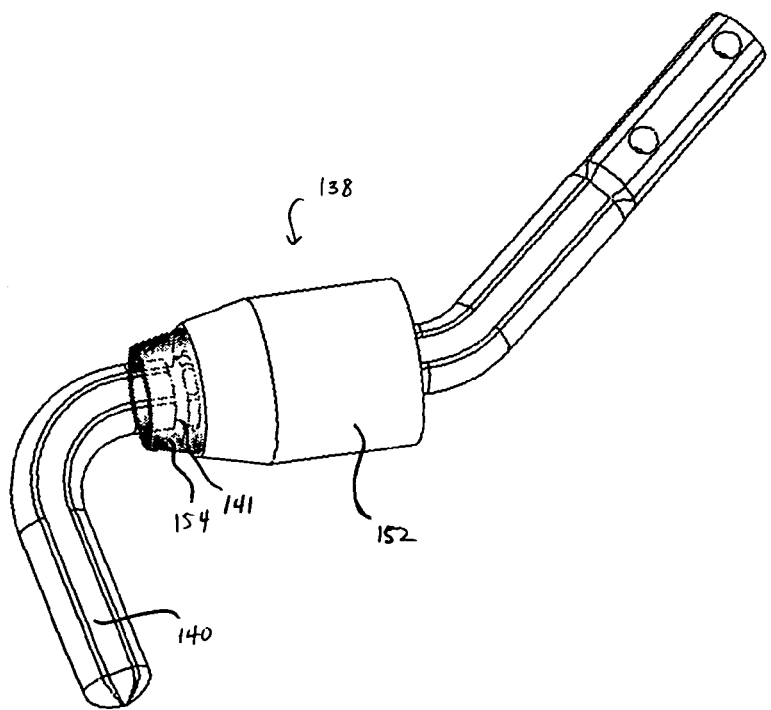
Figure 4C:
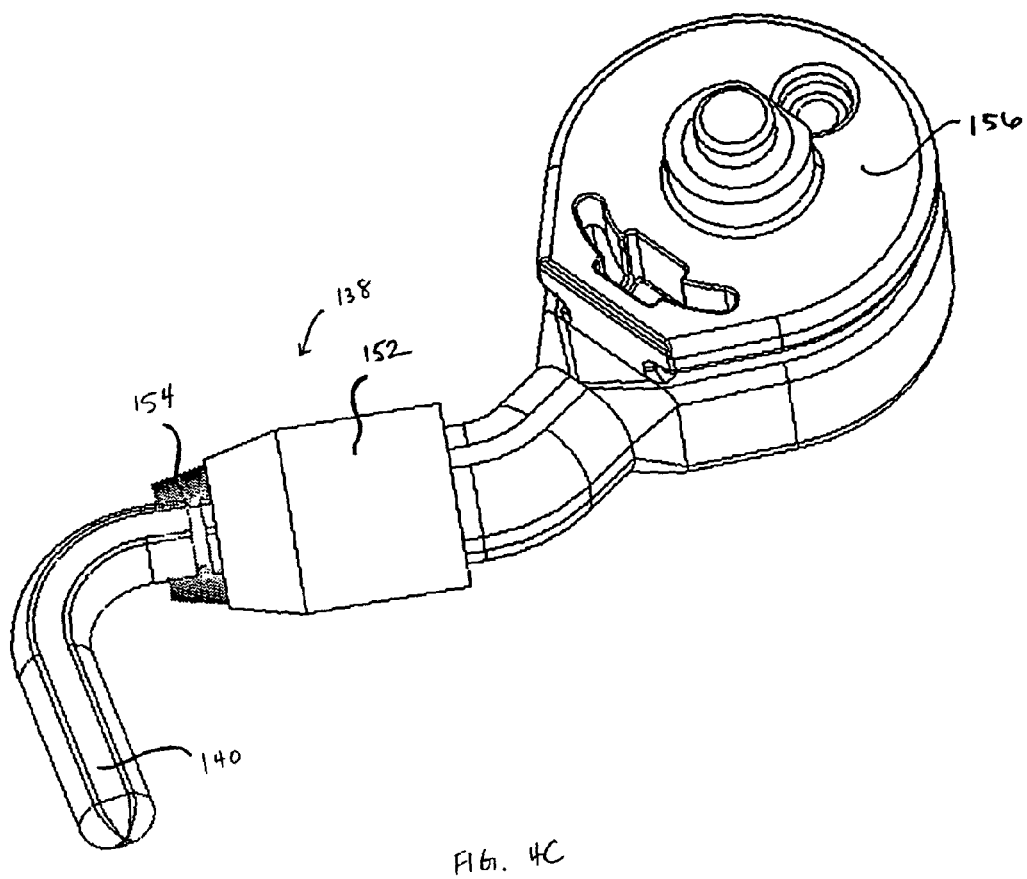
Figure 4D:
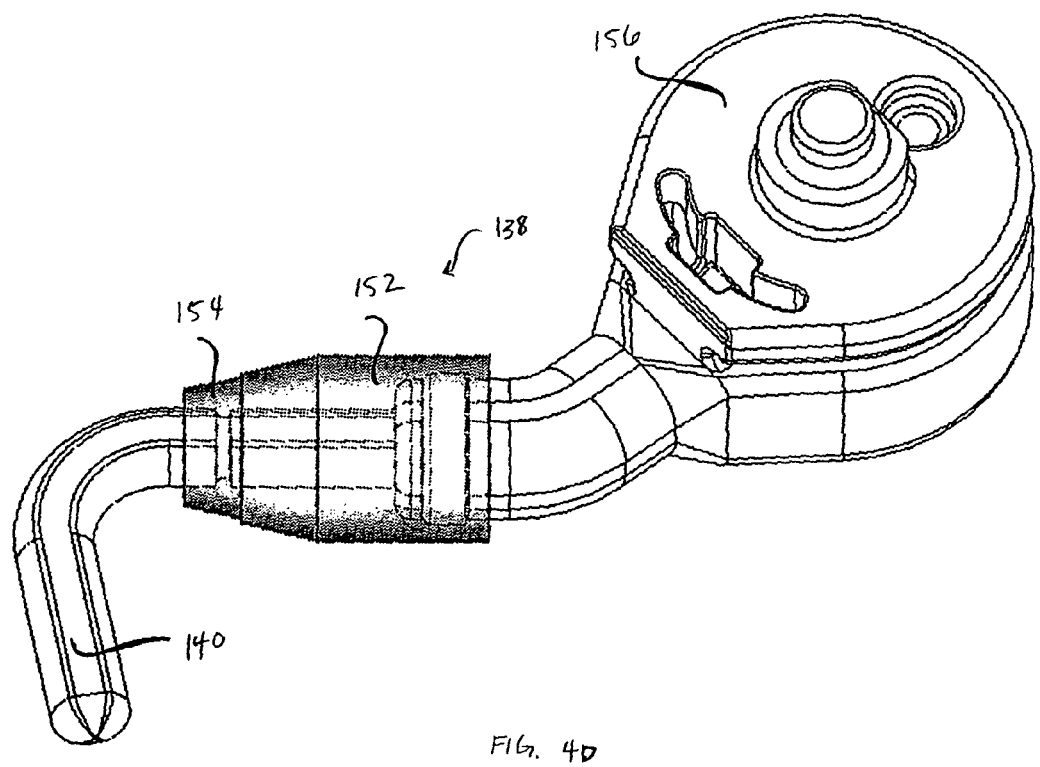

With reference to FIGS. 4A-4D, a method of applying insulation materials to an end-effector according to one embodiment is shown. Generally, insulation material(s) may be applied to end-effector via any suitable method or combination of methods, such as welding, shrink welding, shrink wrapping, laser welding, bonding with epoxy or other adhesive(s), soldering, glass soldering, plasma sputtering of ceramic material, arc spraying of ceramic material, molding and/or the like. In the embodiment shown in FIGS. 4A-4D, a method referred to as "glass soldering" is shown. FIG. 4A shows active electrode 140, in the form of a hook, having a groove 141 in its surface. In FIG. 4B, it can be seen that a glass insulator 154 may be pre-molded to fit over groove 141 and may then be soldered onto active electrode 140. A ceramic insulator 152 may then be positioned over active electrode 140 just proximal to glass insulator 154. In FIG. 4C, a pulley insert 156 may next be molded to active electrode 140 proximal to ceramic insulator 152, thus acting to secure ceramic insulator between pulley insert 156 and glass insulator 154. FIG. 4D, shows various elements transparently, so that pulley insert 156 can be seen fully. Of course, this is only one of many possible embodiments of an insulated end-effector and a method for making such an end-effector. Any other suitable method is contemplated within the scope of the invention.

Figure 5A:
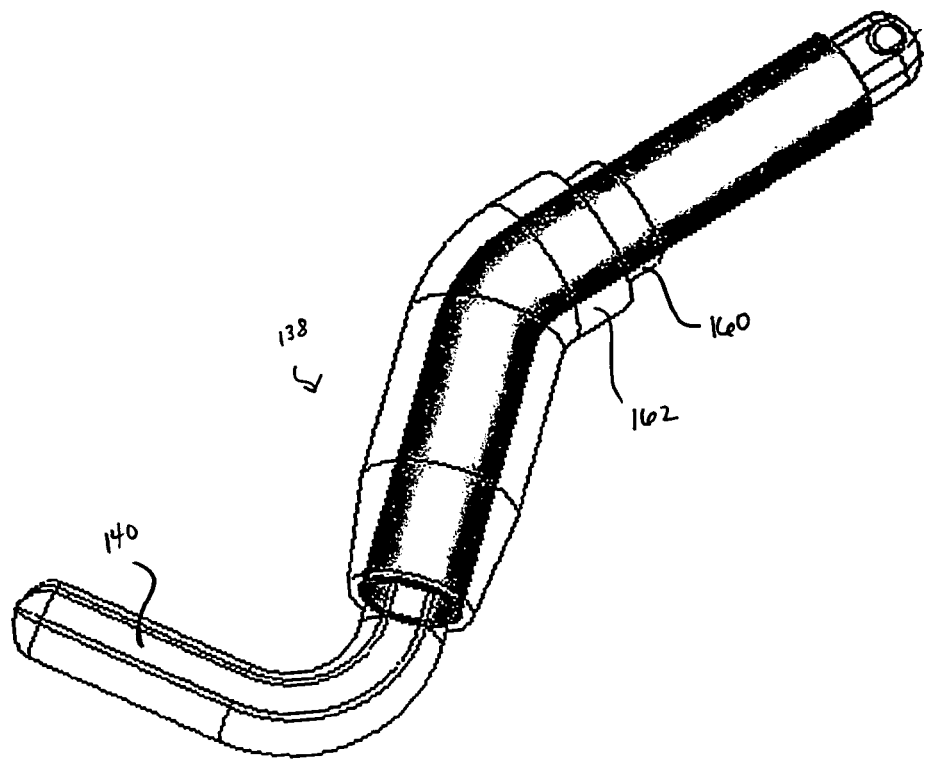
FIGS. 5A-5B are perspective illustrations of an insulated end-effector device in various stages of manufacture, in accordance with another embodiment of the present invention.
Figure 5B:
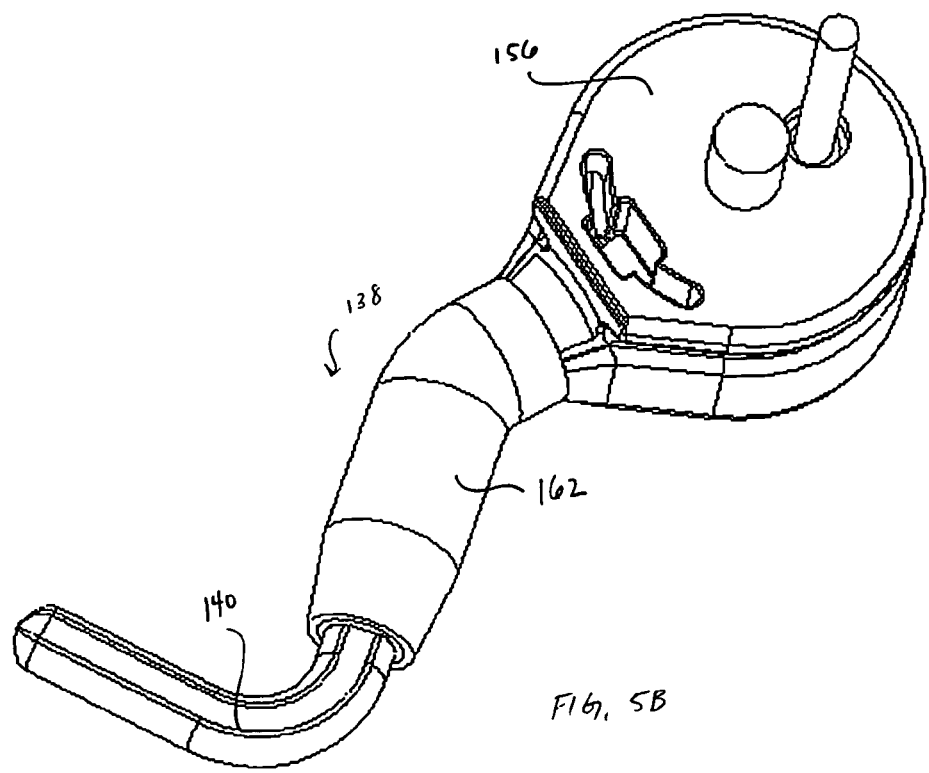

FIGS. 5A-5B show another possible embodiment of active electrode 140 partially covered with a first insulation layer 160 and a second insulation layer 162. In this embodiment, a ceramic material may be applied to active electrode 140 as first layer 160 by any suitable means, such as plasma sputtering, arc spray and/or the like. Such methods may result in first layer 160 having any suitable shape, pattern, thickness, and the like. In one embodiment, for example, arc spraying may be used to apply a ceramic first insulation layer having a thickness of about 0.015 inches. Of course, many other thicknesses are possible. Second insulation layer 162, in some embodiments, may comprise any suitable material disposed over all or part of first layer 160, part of active electrode 140 or both.

In one embodiment, second layer 162 comprises an FEP material, which may be molded over first layer 160 by any suitable method. The FEP second layer 162 will typically help prevent arcing of an electric current proximally in a wet or aqueous environment, as will often be encountered at a surgical site in a patient. Thus, first layer 160 generally prevents proximal conduction of electrical conduction from active electrode 140, and second layer 162 enhances this prevention process, specifically by further preventing current arcing. In some embodiments, such as that just described with a ceramic first layer 160 and an FEP second layer 162, an insulated active electrode 140 may be autoclaved for sterilization purposes (for example withstanding temperatures of about 135° F.) without adversely affecting the insulation layers. FIG. 5B again shown that pulley insert 156 (or any other suitable proximal insert) may then be applied to the proximal end of active electrode 140 by any suitable methods, such as molding. Pulley insert 156 serves its own mechanical function and also may help secure first layer 160 and/or second layer 162 in position on active electrode 140.

As mentioned previously, many embodiments of end-effectors may be manufactured such that they are either permanently attached to surgical instrument 128 or removably coupleable with surgical instrument 128. The latter, removably coupleable end-effectors may have several advantages. For example, some end-effectors may be suitable for a limited number of procedures while the rest of the surgical instrument may be used for many more procedures. Sometimes it may be desirable to change end-effectors during a procedure or between procedures, and it might be easier to simply replace the end-effector, rather than the whole instrument. Removable, disposable end-effectors may also help prevent cross-contamination of patients which might occur if a reusable end-effector is not properly cleaned. Several embodiments of removably coupling end-effectors are described below, and any other suitable embodiment of such an end-effector is contemplated within the scope of the invention.

Figure 6A:
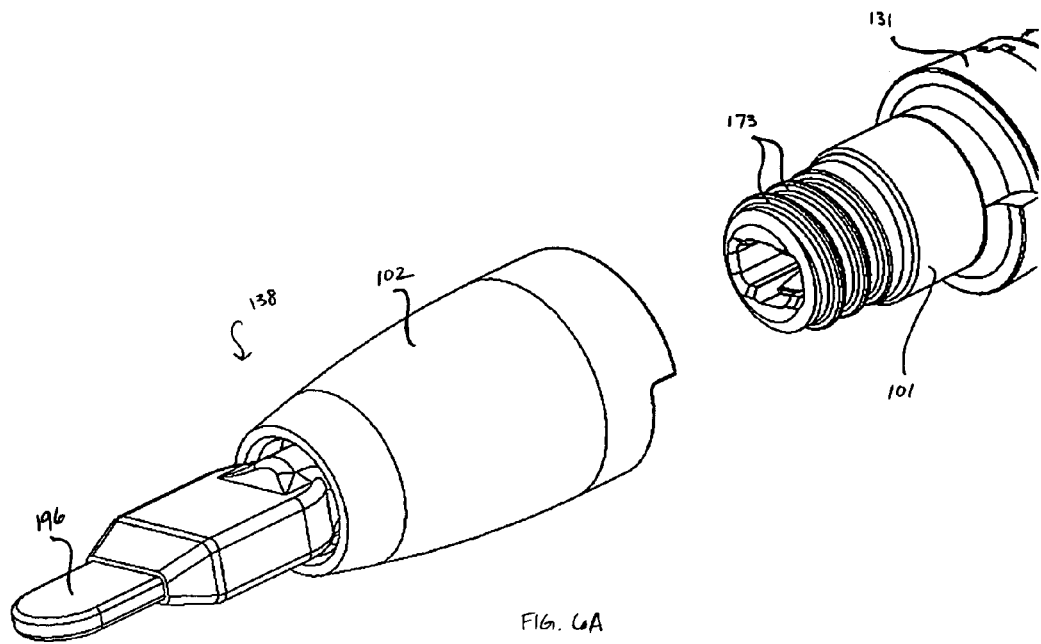
FIGS. 6A-6F are perspective illustrations of an end-effector removably coupling with a distal end of a robotic surgical instrument, in accordance with one embodiment of the present invention.
Figure 6B:
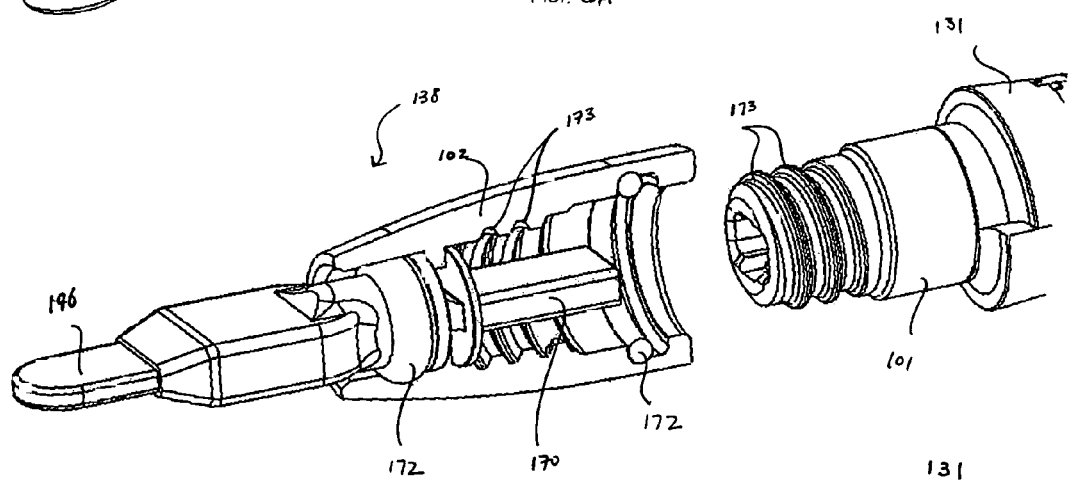
Figure 6C:
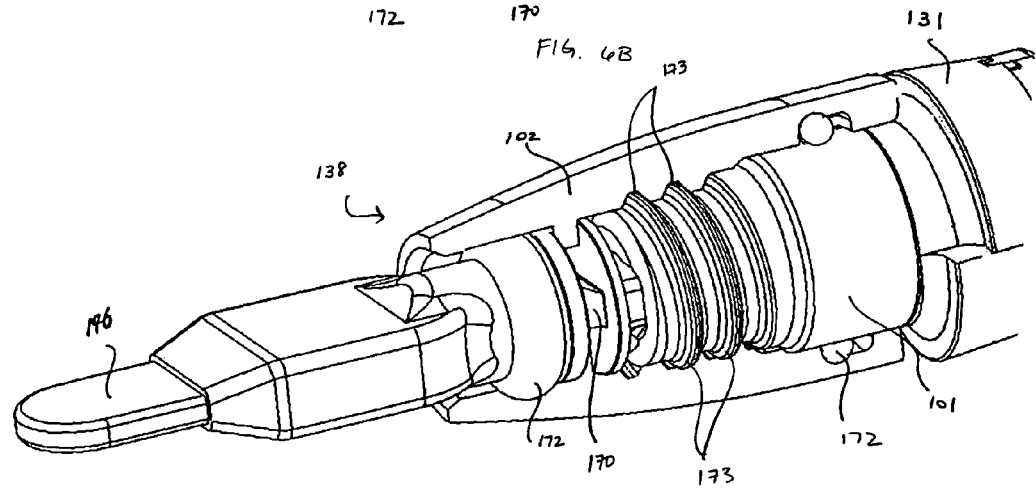

Turning now to FIGS. 6A-6E, one embodiment of a removably coupleable end-effector 138 comprising a "spatula" electrode 196 is shown, first in perspective view then in cross-section, as it is coupled with the distal end 131 of a surgical instrument. FIG. 6A shows that one embodiment includes complimentary threads 173 on a mating component 101 permanently attached to the distal end of the shaft 131 (or wrist 100) of the electrical instrument 128 and within an end-effector sleeve 102 such that the distal end 131 and end-effector 138 may be screwed together. Such an attachment, via threads 173, may typically be made without the use of any attachment tool or other attachment device. Complementary threads 173 can be seen further in FIG. 6B, which also shows that end-effector 138 may include one or more internal sealing rings 172 and an electrical connector 170. Sealing rings 172 are generally polymer rings (or ring(s) of any other suitable material) housed within end-effector 138, which form a water-tight seal when end-effector 138 is coupled with distal end 131 (FIG. 6C). Thus, sealing rings 172 generally prevent water, bodily fluids and/or the like from entering into end-effector 138 when it is coupled with instrument 128. Such fluids may adversely affect operation of, or even damage, an end-effector 138. Generally, any number, size, shape, combination or the like of sealing rings 172 or other sealing devices may be used. Electrical connector 170 provides for electrical connection of end-effector 138 to distal end 131 of instrument 128. Several exemplary embodiments of such electrical connectors will be described in further detail below, but generally electrical connector 170 may have any size, shape, configuration or the like, and may be made of any suitable material.

Figure 6D:
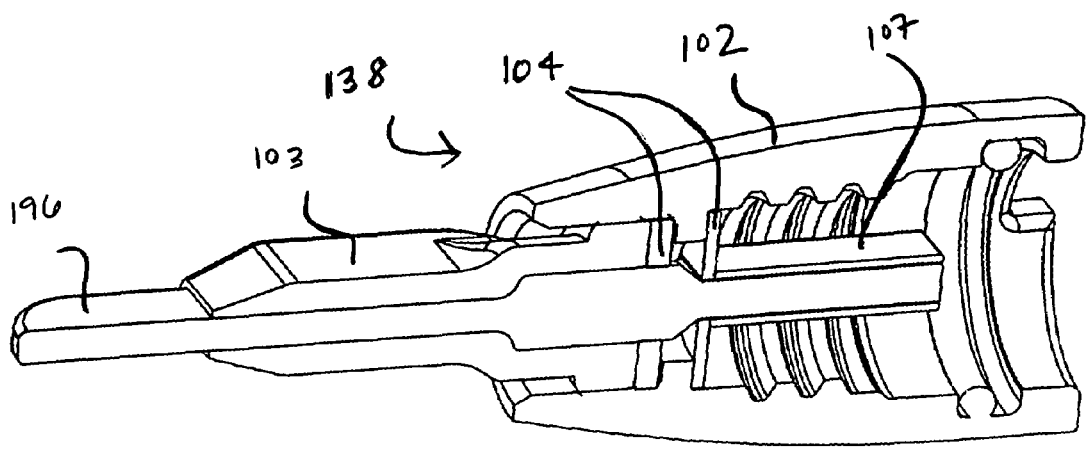
Figure 6E:
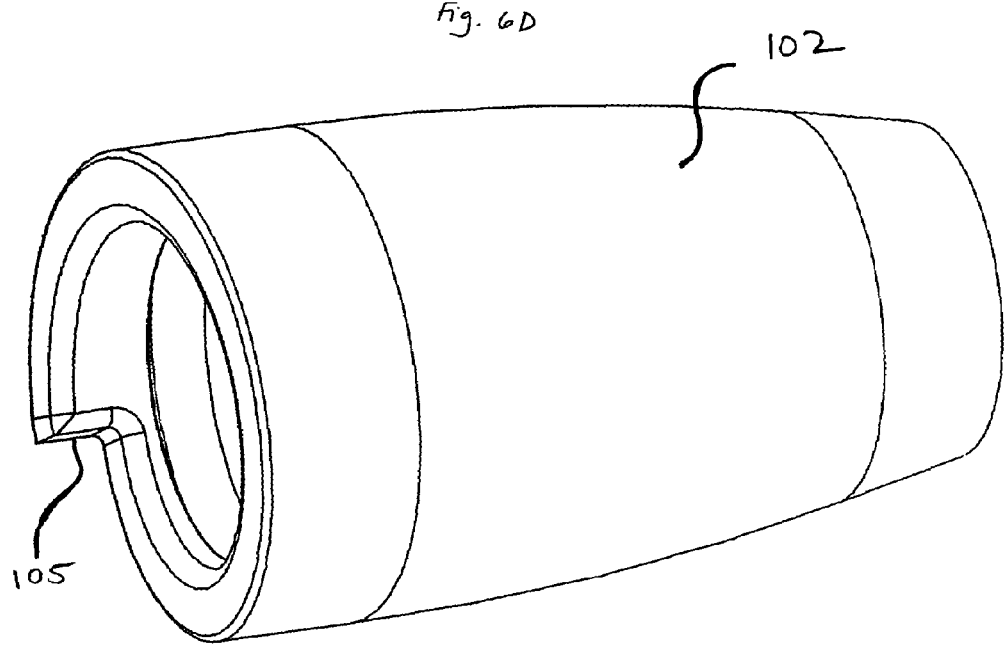
Figure 6F:
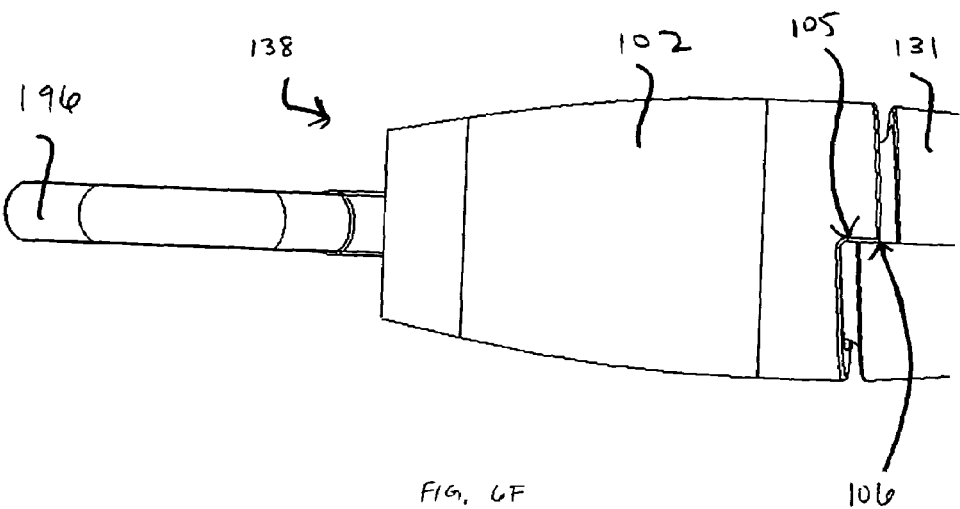

FIG. 6D further illustrates a cross-sectional view of the spatula end-effector 138. It will be appreciated that electrical isolation of the electrosurgical instrument 128, particularly the wrist 100, is accomplished by insulation as well as sealing of outside fluids from the internal electrical connections. Insulator 103 serves as primary insulation while the end-effector sleeve 102 further provides secondary insulation for inhibiting undesirable conduction. The sleeve 102 may further rotate freely about the active electrode. The seal between the primary insulator 103 and the spatula 196 or between the insulating layers 103, 102 may be effected by a silicone adhesive or over-molding process so as to seal the electrical connection. Washers 104 may be utilized to center the active electrode 196, 140 within the sleeve 102 and maintain its positioning (i.e., prevent movement of the electrode in the presence of side loads or pulling). Further an electrical connector box 107 within the sleeve 102 further ensures that the electrode is centered and secured. FIGS. 6E and 6F further illustrate that the mechanical coupling of the end-effector may include a helical feature 105, 106 on the sleeve 102 and the distal end 131 that stop rotation of the sleeve 102 upon engagement.

Figure 7A:
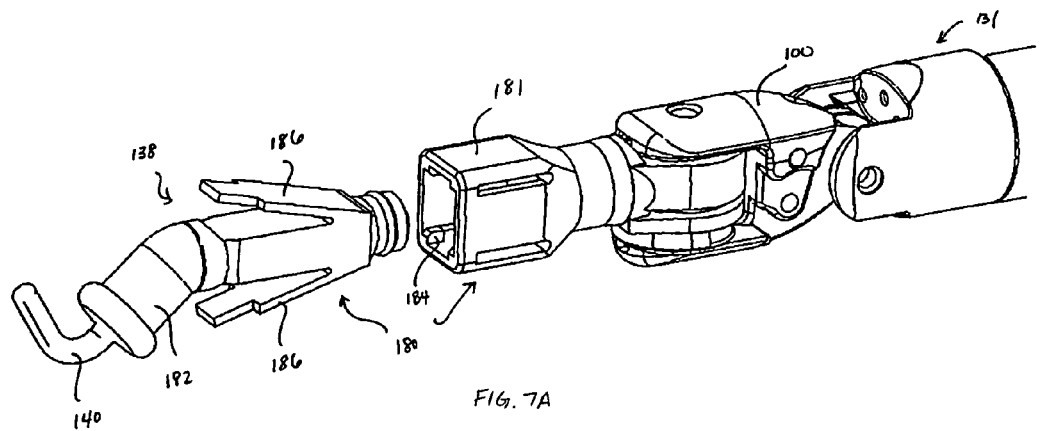
FIGS. 7A-7B are perspective illustrations of an end-effector removably coupling with a distal end of a robotic surgical instrument, in accordance with another embodiment of the present invention.
Figure 7B:
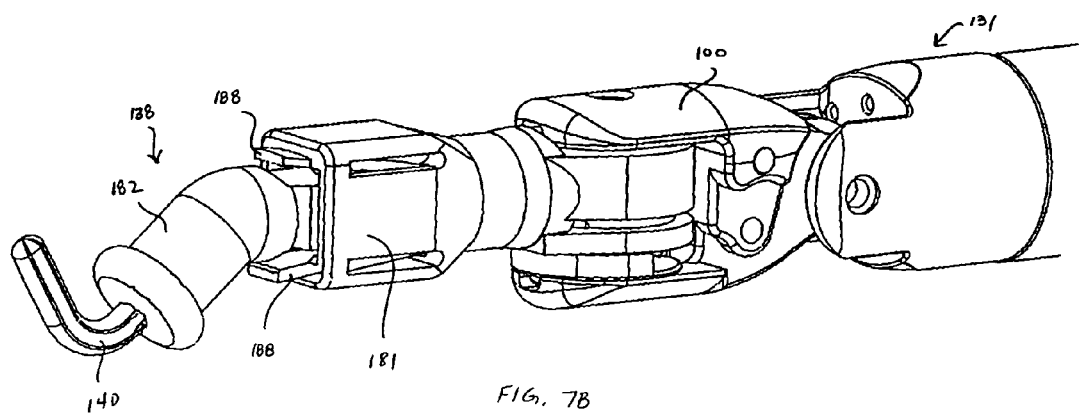

FIGS. 7A and 7B show another embodiment of end-effector 138 removably coupleable with distal end 131 of instrument 128. Here, end-effector 138 is shown with an insulator 182 in place and is coupled with distal end 131 via a spring latch mechanism 180. Spring latch mechanism 180 includes two spring tabs 186 on end-effector 138 which fit into a housing 181 permanently attached to the distal end of the shaft 131 (or wrist 100) of the electrical instrument 128. The internal surface of housing 181 includes multiple protrusions 184 for catching on portions of spring tabs 186 to secure end-effector 138 within housing 181. Of course, any number and configuration of protrusions 184 may be used. As shown in FIG. 7B, when end-effector 138 is inserted into housing 181 it will eventually snap or lock into place, with spring tabs 186 locked/secured behind protrusions 184. In some embodiments, as shown, spring tabs 186 may each have a protruding distal end 188 that protrudes out of housing 181. Such protruding distal ends 188 would allow a user to grab onto tabs 186 to pull end-effector 138 out of housing 181 when a procedure is complete or when otherwise desired. Generally, such a spring latch mechanism 180 may have any suitable size, shape or configuration and may be made of any suitable material or combination of materials, such as polymers, polypropylene, stainless steel or the like.

Figure 8A:
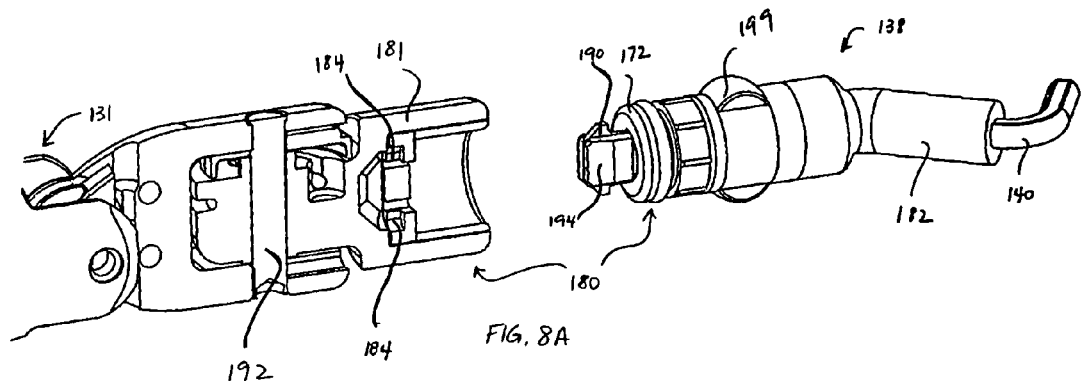
FIGS. 8A-8C are perspective illustrations of an end-effector removably coupling with a distal end of a robotic surgical instrument, in accordance with other embodiments of the present invention.
Figure 8B:
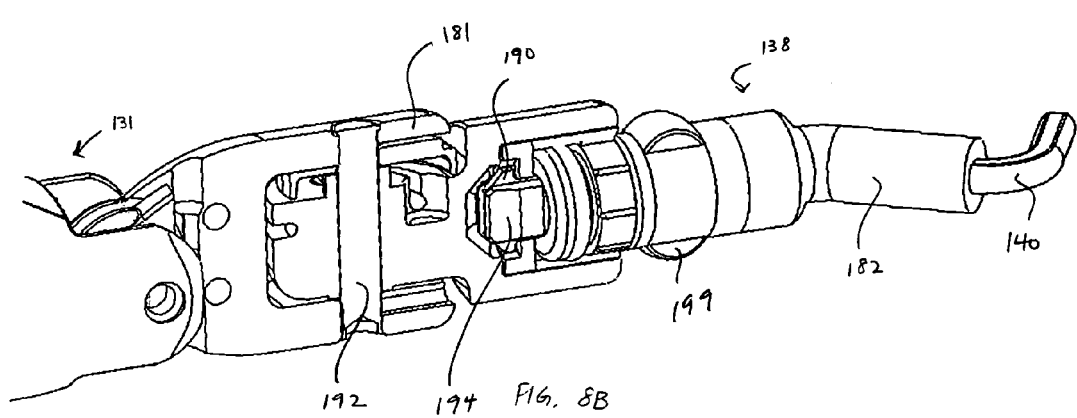
Figure 8C:
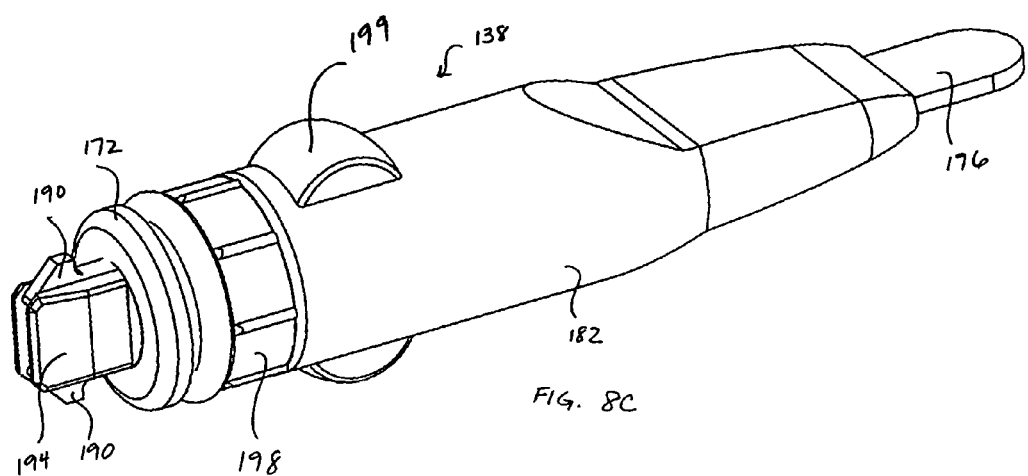

With reference now to FIGS. 8A-8C, alternate embodiments of a latch connection mechanism 180 are shown. As shown in FIG. 8A, some embodiments of end-effector 138 may include a proximal latch member 190 that is coupled with or includes an electrode 194 or other electrical connector. Latch member 190 acts to secure end-effector 138 within housing 181 by latching behind protrusions 184 in housing 181, while electrode 194 provides for electrical connection between end-effector 138 and instrument 128. Buttons 199 allows for disengagement of the end-effector 138 from the instrument 128. Again, end-effector 138 may also include one or more sealing rings 172 for creating a water-tight seal with distal end 131 of instrument 128. FIG. 8B shows end-effector 138 and distal end 131 coupled together. In both figures, housing 181 includes a cross pin 192, which may be made of stainless steel or any other suitable material and which generally provides stability to distal end 131.

FIG. 8C shows yet another embodiment of a removably coupleable end-effector 138, again with a latch member 190 for coupling with a distal end of a surgical instrument. This embodiment emphasizes the fact that any suitable type, size, shape or form of active electrode may be included in end-effector 138, as here the active electrode comprises a "spatula" electrode device 196. Another optional feature of end-effector 138 is an attachment ring 198, which is generally a textured surface ring around a portion of end-effector 138 that enhances ease of coupling and removal of end-effector 138 from the distal end of the instrument. The textured surface further may increase stability of the latch member attachment. The buttons 199 may be de-pressed manually or alternatively by a grasper, needle driver, etc. to compress the ring 198 which in turn compresses the latches 190 for disabling.

Figure 9C:
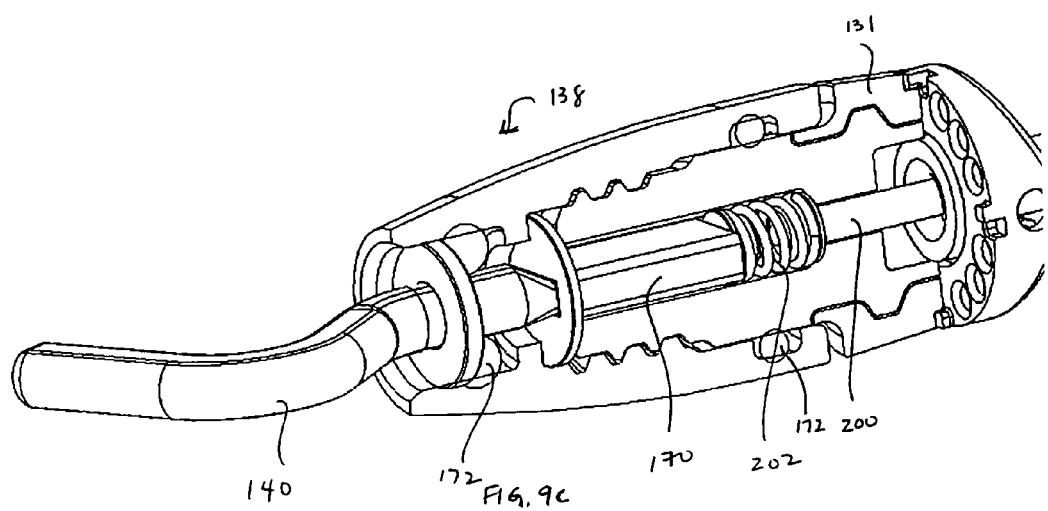
FIGS. 9A-9C are perspective illustrations of an end-effector removably coupling with a distal end of a robotic surgical instrument, showing the electrical connection between the end-effector and the instrument, in accordance with one embodiment of the present invention.
Figure 9A:
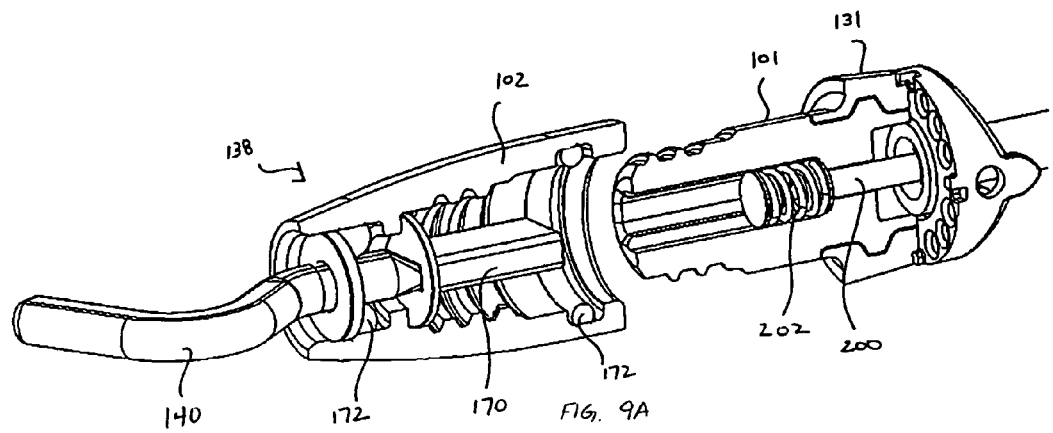
Figure 9B:
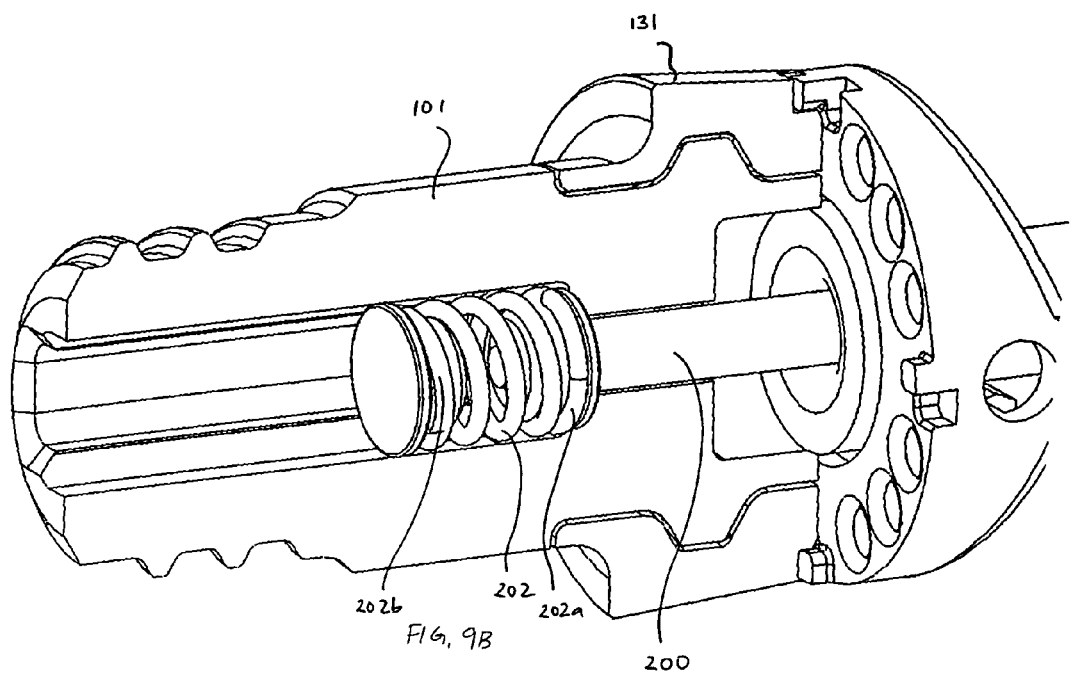

Referring now to FIGS. 9A-9C, one embodiment of an electrical connection between end-effector 138 and distal end 131 is shown. End-effector 138 is similar to embodiments shown previously and includes electrical connector 170. Distal end 131 includes an electrical transmission member 200 coupled with a spring member 202. As shown in FIG. 9B, spring member 202 is coupled at its proximal end 202a with electrical transmission member 200 and is free at its distal end 202b, such that it may be coupled with electrical connector 170 or any other suitable electrical connection means on end-effector. As shown in FIG. 9C, when end-effector 138 is coupled with distal end 131, such as via complementary threads, electrical connector 170 presses against spring member 202 to form an electrical connection between end-effector 138 and distal end 131.

Figure 10A:
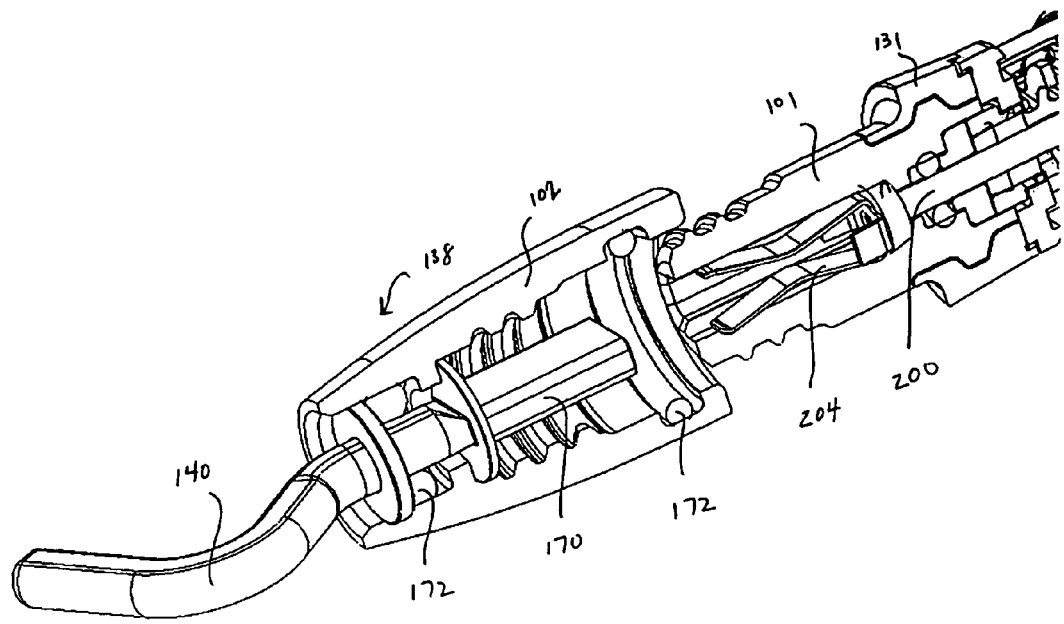
FIGS. 10A-10E are perspective illustrations of an end-effector removably coupling with a distal end of a robotic surgical instrument, showing the electrical connection between the end-effector and the instrument, in accordance with another embodiment of the present invention.
Figure 10B:
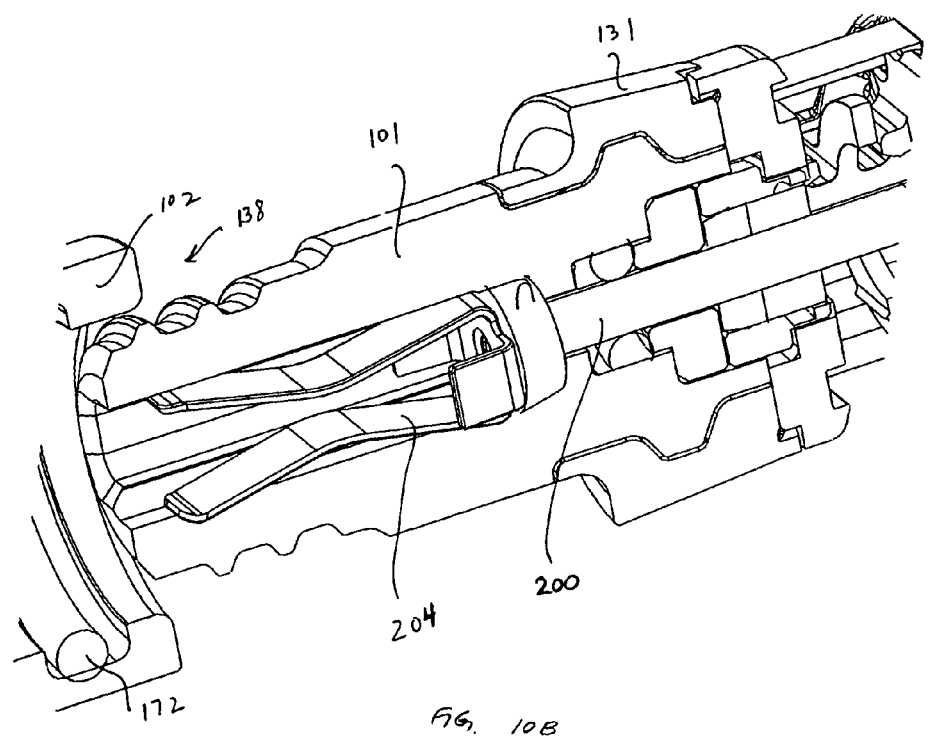
Figure 10C:
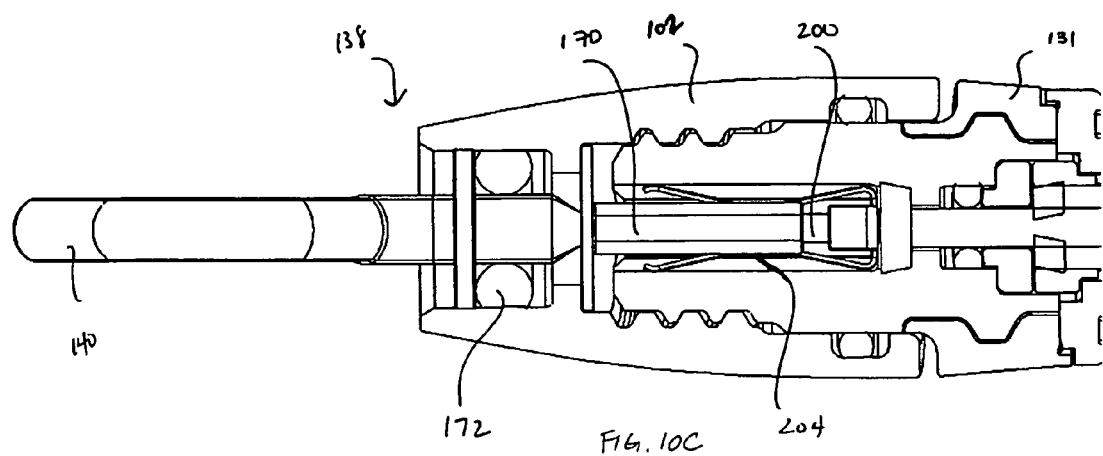
Figure 10E:
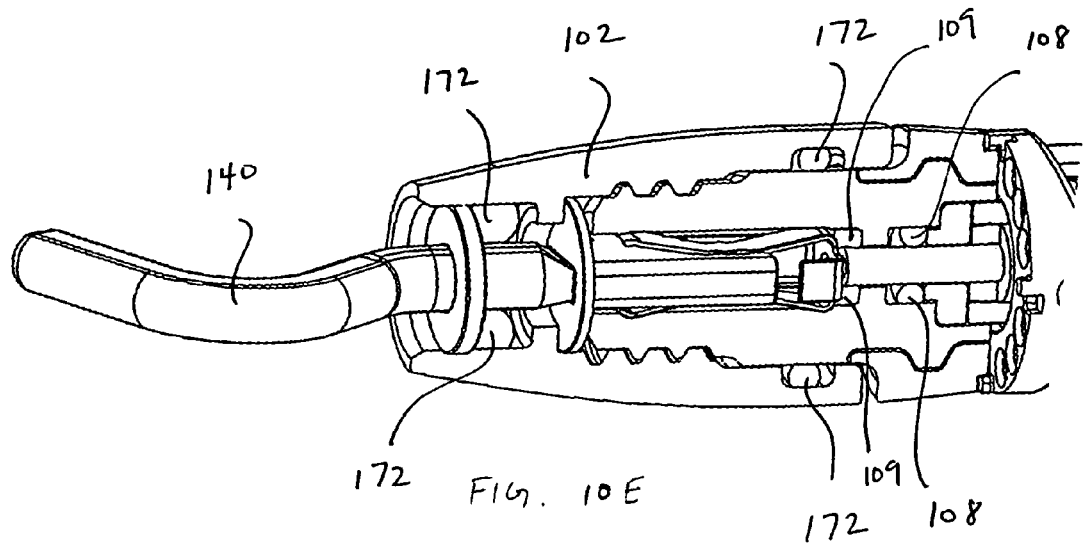
Figure 10D:
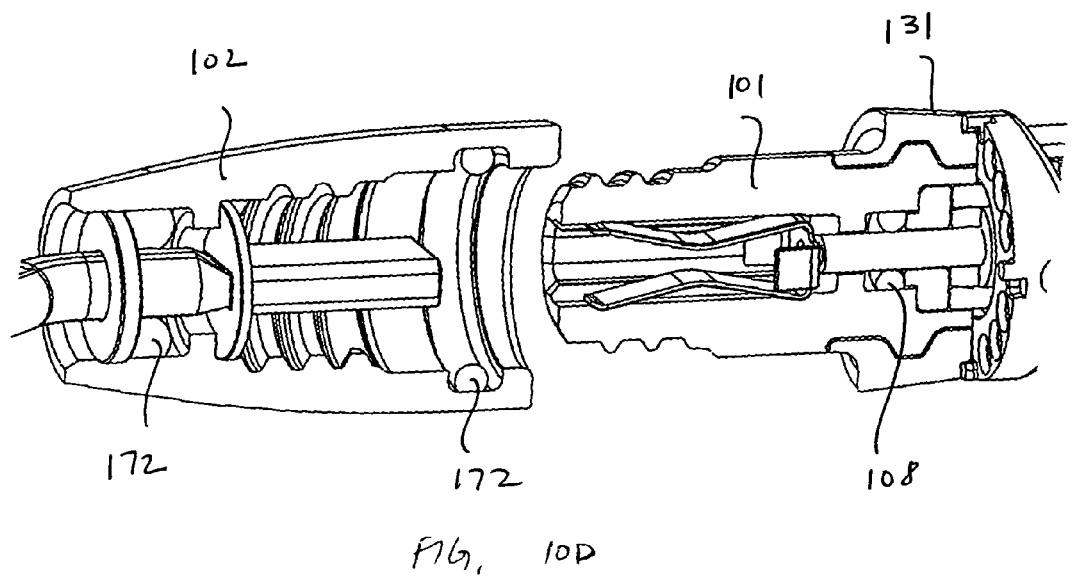

Any other suitable electrical connection between end-effector 138 and distal end 131 of instrument 128 may be used, and another exemplary embodiment is shown in FIGS. 10A-10C. In this embodiment, the spring member is replaced with a gripping member 204. Gripping member 204 is shaped so as to grip electrical connector 170 between its two arms when end-effector 138 is coupled with distal end 131, thus creating the electrical connection to provide electrical energy to active electrode from electrical transmission member 200. This embodiment further cleans away any oxidation build up that may have accumulated on any of the contact surfaces. FIGS. 10D and 10E illustrate that electrical isolation of the electrosurgical instrument 128, particularly the wrist 100, is accomplished in part by sealing. O-rings 172 and silicone potting 109 associated with the end-effector sleeve 102 as well as additional O-rings 109 in the distal end of the shaft 131 further seal the electrical connection. Additionally, as shown in FIGS. 9A and 9C, sealing is effected prior to any electrical contact as an additional safety feature.

Figure 11C:
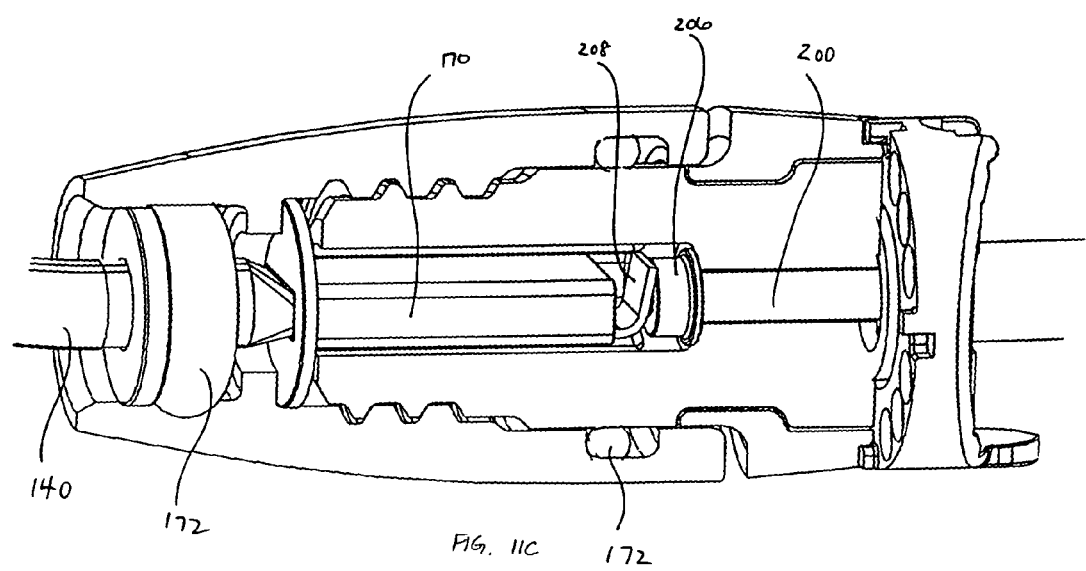
FIGS. 11A-11C are perspective illustrations of an end-effector removably coupling with a distal end of a robotic surgical instrument, showing the electrical connection between the end-effector and the instrument, in accordance with yet another embodiment of the present invention.
Figure 11A:
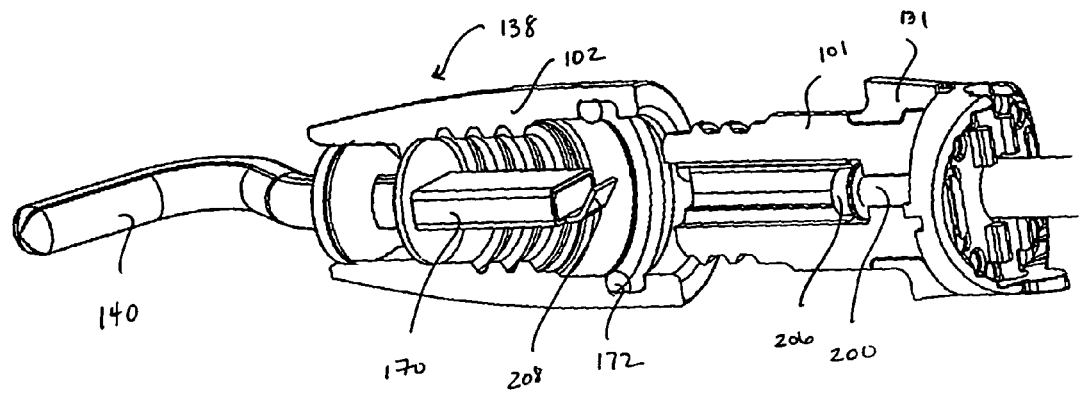
Figure 11B:
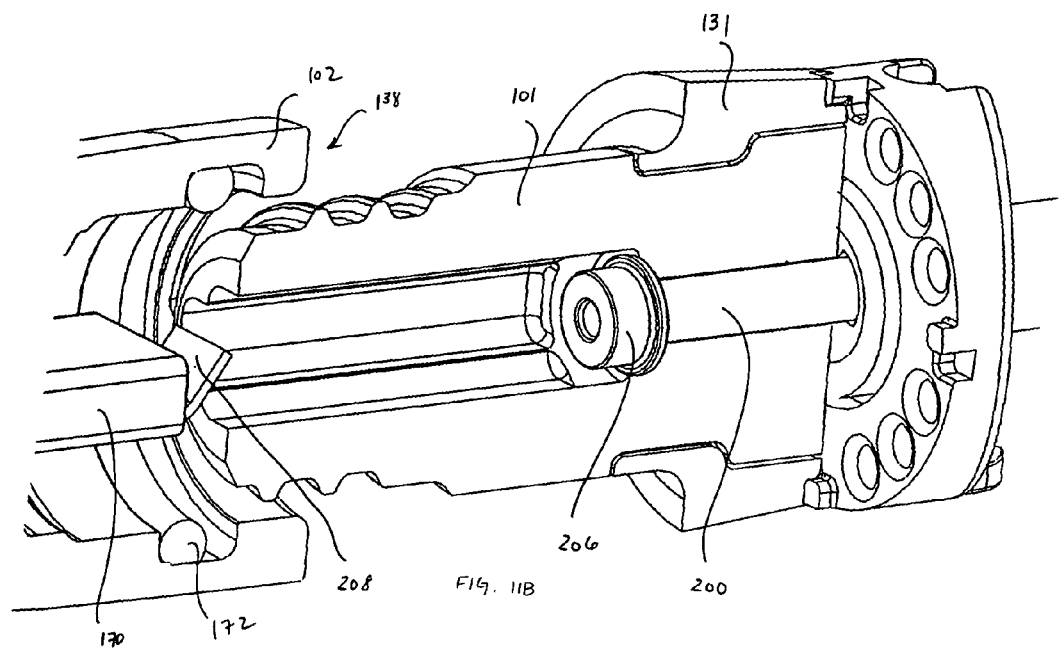

FIGS. 11A-11C show another embodiment of an electrical connection between end-effector 138 and distal end 131 of instrument 128. In this embodiment, end-effector includes an electrical tab 208 coupled with the proximal end of electrical connector 170. Electrical tab 208 is designed to press against an electrical platform 206 in distal end 131 when end-effector 138 and distal end 131 are coupled together. As shown in FIG. 11C, tab 208 may be sufficiently flexible or bendable so that when it engages with electrical platform 208, it bends. Electrical platform 208, in turn, may be either rigid or spring loaded in various embodiments.

Figure 12A:
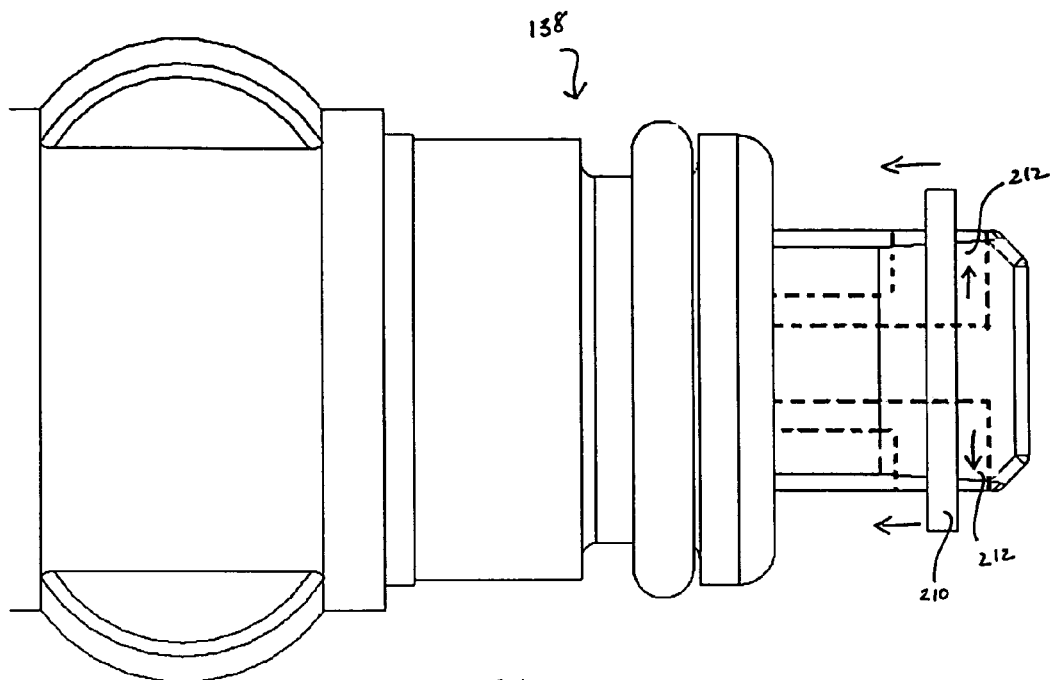
FIGS. 12A-12D are perspective illustrations of part of an end-effector having a lockout ring for preventing reuse, in accordance with one embodiment of the present invention.
Figure 12B:
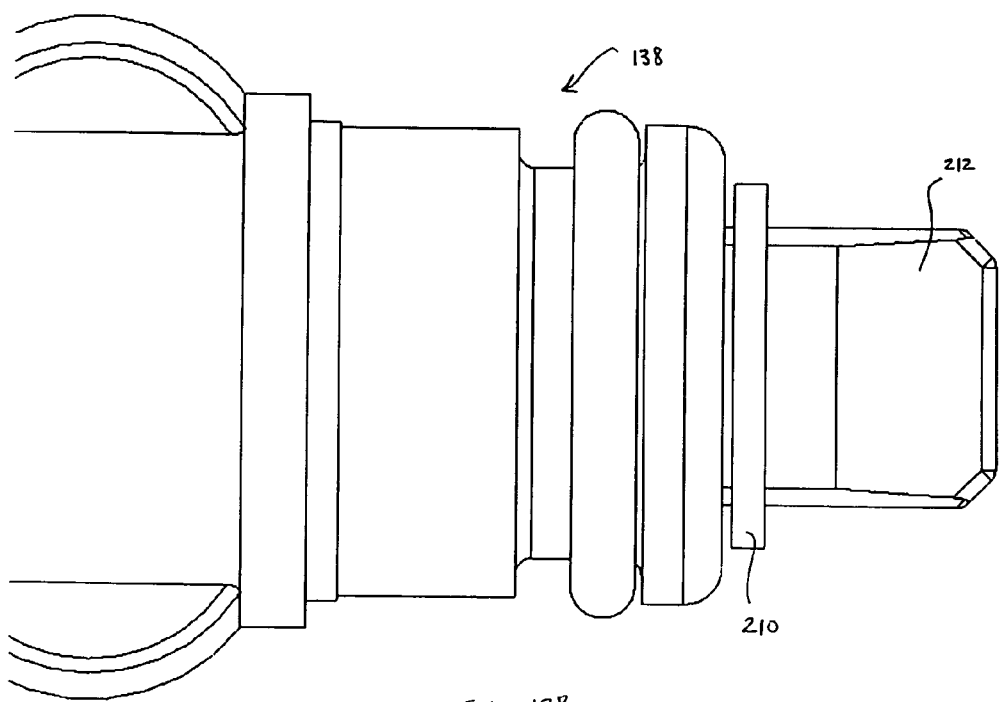
Figure 12C:
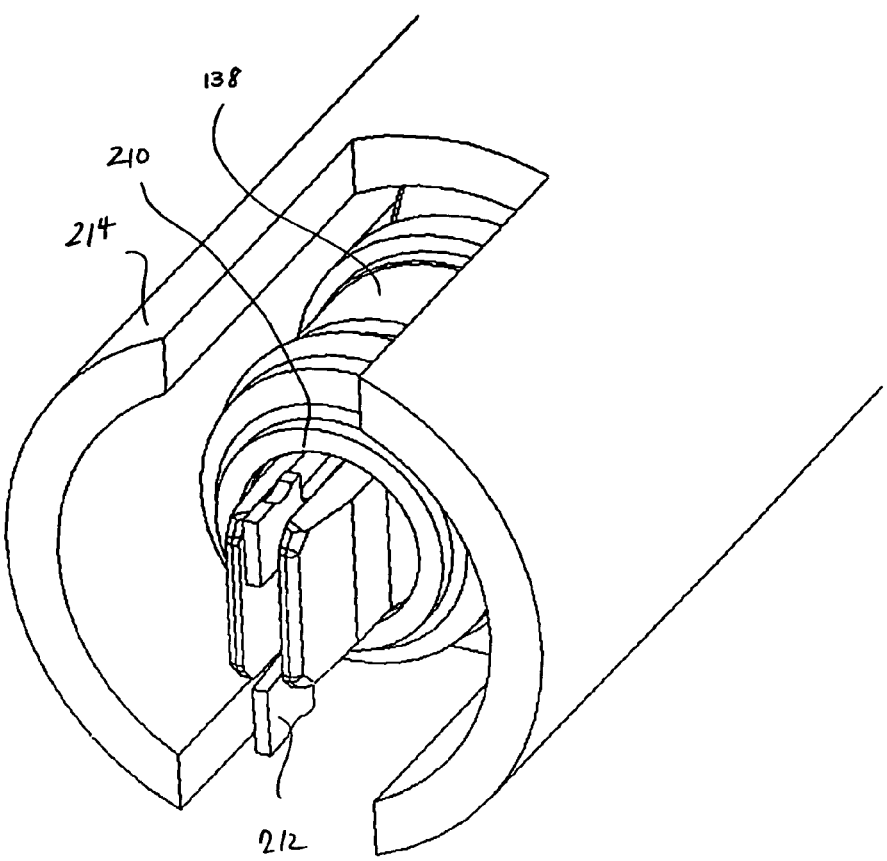
Figure 12D:
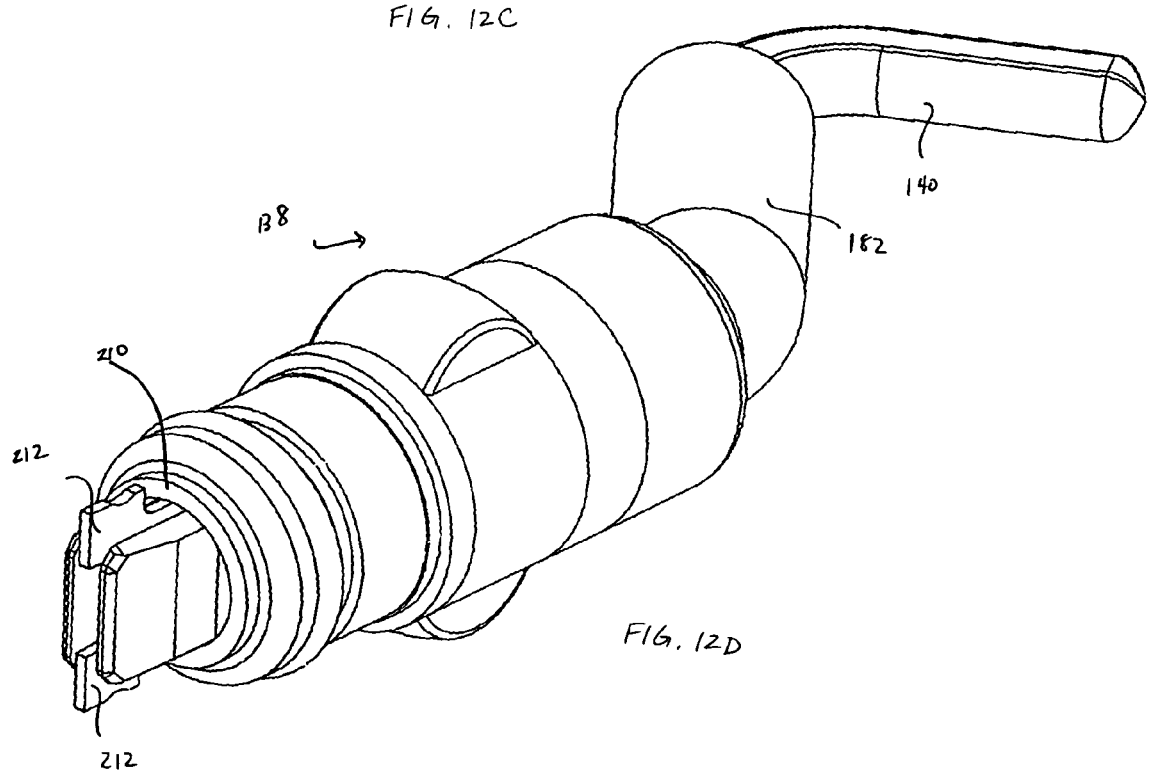

As mentioned above, it may sometimes be advantageous to have end-effectors which are disposable and which are disabled after one use or a number of uses. FIGS. 12A-12D show one embodiment of such a disposable, disablable end-effector 138. In this embodiment, the proximal end of end-effector 138 includes one or more shape memory tabs 212 which are held in a confined position by a lockout ring 210. As shown in FIG. 12A, if lockout ring 210 is moved proximally (arrows pointing to left) shape memory tabs 212 deploy—i.e., are allowed to expand (arrows pointing up and down). A distal end of a surgical instrument could be designed so as to move lockout ring 210 proximally when end-effector 138 is coupled with the instrument. The distal end of the instrument may also be designed such that it cannot couple with end-effector 138 once shape memory tabs 212 are deployed, expanded or the like, thus preventing reuse of a disposable end-effector. FIG. 12B shows a perspective view of such an embodiment, and FIG. 12C shows the embodiment housed within a protective outer housing 214 for storage, transport and the like. FIG. 12D shows how, when lockout ring 210 is moved proximally, shape memory tabs (or tab) 212 expand to prevent further coupling of end-effector 138 with a surgical instrument. Of course, many other embodiments of a disposable end-effector with means for preventing reuse are possible, and all such embodiments are contemplated within the scope of the invention.

Referring now to FIG. 13, end-effector 138 is shown coupled with an embodiment of a packaging tab 216 for protecting the active electrode and protective outer housing 214 for protecting an area around lockout ring 210 and shape memory tabs 212. Tab 216 and protective outer housing 214 may be used to house end-effector 138 during storage, transport of the device and/or the like.

Although the invention has been described above with specific reference to various embodiments and examples, it should be understood that various additions, modifications, deletions and alterations may be made to such embodiments without departing from the spirit or scope of the invention. Accordingly, it is intended that all reasonably foreseeable additions, deletions, alterations and modifications be included within the scope of the invention as defined in the following claims.

What is claimed is:

1. An end-effector device for use with an electrosurgical instrument for performing a minimally invasive surgical procedure, the end-effector device comprising:
   an electrode;
   a mechanism including at least one spring tab adapted to snap fit into a housing of an electrosurgical instrument for coupling the electrode to the electrosurgical instrument;

an insulative rigid sleeve disposed at least partially around the electrode so as to inhibit surface conduction of electrical current flowing from the electrode to the electrosurgical instrument;

first and second internal sealing rings respectively compressed against inner distal and proximal ends of the insulative rigid sleeve and disposed so as to inhibit fluid from entering into an interior of the insulative rigid sleeve through respectively the inner distal and proximal ends and making contact with any portion of the electrode disposed therein during a minimally invasive surgical procedure; and an insulation layer disposed at least partially around the electrode and one of the first and second internal sealing rings so as to additionally inhibit fluid from entering into the interior of the insulative rigid sleeve and making contact with any portion of the electrode disposed therein during the minimally invasive surgical procedure.

2. The end-effector device as in claim 1, wherein the electrode comprises a scalpel blade, a beaver blade, a hook, a spatula, movable jaws, scissors, a needle point, hockey stick, dissectors, or a probe.

3. The end-effector device as in claim 1, wherein the electrode transmits radiofrequency energy during the minimally invasive surgical procedure.

4. The end-effector device as in claim 1, wherein at least one of the first and second internal sealing rings comprises an o-ring.

5. The end-effector device as in claim 1, wherein the end-effector device is constructed so as to be disposable.

6. The end-effector device as in claim 1, wherein the coupling mechanism is configured so as to be incapable of re-coupling to the electrosurgical instrument after once being coupled to and uncoupled from the electrosurgical instrument.

7. The end-effector device as in claim 1, wherein the coupling mechanism effectively permanently couples the device with the electrosurgical instrument.

8. The end-effector device as in claim 1, wherein the insulation layer comprises ceramic material, glass, silicone, polypropylene, fluoropolymer, or insulating plastic.

9. The end-effector device as in claim 8, wherein the insulative rigid sleeve comprises ceramic material, glass, silicone, polypropylene, fluoropolymer, or insulating plastic.

10. The end-effector device as in claim 8, wherein the insulation layer comprises a first insulation material completely encircling part of the electrode, and wherein the insulative rigid sleeve comprises a second insulation material completely encircling the first insulation material and abutting the electrosurgical instrument.

11. An end-effector device for use with an electrosurgical instrument for performing a minimally invasive surgical procedure, the end-effector device comprising:

an electrode;

a mechanism including an electrical connector for electrical connection with a transmission member via a coil shaped spring member of an electrosurgical instrument for coupling the electrode to the electrosurgical instrument;

an insulative rigid sleeve disposed at least partially around the electrode so as to inhibit surface conduction of electrical current flowing from the electrode to the electrosurgical instrument;

first and second internal sealing rings respectively compressed against inner distal and proximal ends of the insulative rigid sleeve and disposed so as to inhibit fluid from entering into an interior of the insulative rigid sleeve through respectively the inner distal and proximal ends and making contact with any portion of the electrode disposed therein during a minimally invasive surgical procedure; and an insulation layer disposed at least partially around the electrode and one of the first and second internal sealing rings so as to additionally inhibit fluid from entering into the interior of the insulative rigid sleeve and making contact with any portion of the electrode disposed therein during the minimally invasive surgical procedure.

12. The end-effector device as in claim 11, wherein the electrode comprises a scalpel blade, a beaver blade, a hook, a spatula, movable jaws, scissors, a needle point, hockey stick, dissectors, or a probe.

13. The end-effector device as in claim 11, wherein the electrode transmits radiofrequency energy during the minimally invasive surgical procedure.

14. The end-effector device as in claim 11, wherein at least one of the first and second internal sealing rings comprises an o-ring.

15. The end-effector device as in claim 11, wherein the end-effector device is constructed so as to be disposable.

16. The end-effector device as in claim 11, wherein the coupling mechanism is configured so as to be incapable of re-coupling to the electrosurgical instrument after once being coupled to and uncoupled from the electrosurgical instrument.

17. The end-effector device as in claim 11, wherein the coupling mechanism effectively permanently couples the device with the electrosurgical instrument.

18. The end-effector device as in claim 11, wherein the insulation layer comprises ceramic material, glass, silicone, polypropylene, fluoropolymer, or insulating plastic.

19. The end-effector device as in claim 18, wherein the insulative rigid sleeve comprises ceramic material, glass, silicone, polypropylene, fluoropolymer, or insulating plastic.

20. The end-effector device as in claim 18, wherein the insulation layer comprises a first insulation material completely encircling part of the electrode, and wherein the insulative rigid sleeve comprises a second insulation material completely encircling the first insulation material and abutting the electrosurgical instrument.

21. An end-effector device for use with an electrosurgical instrument for performing a minimally invasive surgical procedure, the end-effector device comprising:

an electrode;

a mechanism including an electrical connector for electrical connection with a transmission member via a gripping member of an electrosurgical instrument for coupling the electrode to the electrosurgical instrument, the gripping member having two arms to grip the electrical connector;

an insulative rigid sleeve disposed at least partially around the electrode so as to inhibit surface conduction of electrical current flowing from the electrode to the electrosurgical instrument;

first and second internal sealing rings respectively compressed against inner distal and proximal ends of the insulative rigid sleeve and disposed so as to inhibit fluid from entering into an interior of the insulative rigid sleeve through respectively the inner distal and proximal ends and making contact with any portion of the electrode disposed therein during a minimally invasive surgical procedure; and an insulation layer disposed at least partially around the electrode and one of the first and second internal sealing rings so as to additionally inhibit fluid from entering into the interior of the insulative rigid sleeve and making contact with any portion of the electrode disposed therein during the minimally invasive surgical procedure.

22. The end-effector device as in claim 21, wherein the electrode comprises a scalpel blade, a beaver blade, a hook, a spatula, movable jaws, scissors, a needle point, hockey stick, dissectors, or a probe.

23. The end-effector device as in claim 21, wherein the electrode transmits radiofrequency energy during the minimally invasive surgical procedure.

24. The end-effector device as in claim 21, wherein at least one of the first and second internal sealing rings comprises an o-ring.

25. The end-effector device as in claim 21, wherein the end-effector device is constructed so as to be disposable.

26. The end-effector device as in claim 21, wherein the coupling mechanism is configured so as to be incapable of re-coupling to the electrosurgical instrument after once being coupled to and uncoupled from the electrosurgical instrument.

27. The end-effector device as in claim 21, wherein the coupling mechanism effectively permanently couples the device with the electrosurgical instrument.

28. The end-effector device as in claim 21, wherein the insulation layer comprises ceramic material, glass, silicone, polypropylene, fluoropolymer, or insulating plastic.

29. The end-effector device as in claim 28, wherein the insulative rigid sleeve comprises ceramic material, glass, silicone, polypropylene, fluoropolymer, or insulating plastic.

30. The end-effector device as in claim 28, wherein the insulation layer comprises a first insulation material completely encircling part of the electrode, and wherein the insulative rigid sleeve comprises a second insulation material completely encircling the first insulation material and abutting the electrosurgical instrument.

* * * * *